US009637765B2

(12) United States Patent
Luterbacher et al.

(10) Patent No.: US 9,637,765 B2
(45) Date of Patent: May 2, 2017

(54) BIPHASIC SUPERCRITICAL CARBON DIOXIDE-WATER PRETREATMENT OF LIGNOCELLULOSIC BIOMASS

(75) Inventors: Jeremy Luterbacher, Ithaca, NY (US); Larry P. Walker, Ithaca, NY (US); Jefferson W. Tester, Hingham, MA (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 13/638,338

(22) PCT Filed: Mar. 10, 2011

(86) PCT No.: PCT/US2011/027854
§ 371 (c)(1),
(2), (4) Date: Sep. 28, 2012

(87) PCT Pub. No.: WO2011/126654
PCT Pub. Date: Oct. 13, 2011

(65) Prior Publication Data
US 2013/0017579 A1  Jan. 17, 2013

Related U.S. Application Data

(60) Provisional application No. 61/319,086, filed on Mar. 30, 2010.

(51) Int. Cl.
*C12P 19/02* (2006.01)
*C12P 17/04* (2006.01)

(52) U.S. Cl.
CPC ............ *C12P 19/02* (2013.01); *C12P 17/04* (2013.01); *C12P 2201/00* (2013.01); *Y02E 50/16* (2013.01); *Y02E 50/17* (2013.01); *Y02P 20/544* (2015.11)

(58) Field of Classification Search
None
See application file for complete search history.

(56) References Cited

U.S. PATENT DOCUMENTS

| | | | |
|---|---|---|---|
| 4,995,943 | A | 2/1991 | Rehberg |
| 5,424,417 | A | 6/1995 | Torget et al. |
| 5,705,369 | A | 1/1998 | Torget et al. |
| 2007/0161095 | A1 | 7/2007 | Gurin |
| 2007/0254076 | A1 | 11/2007 | Bobier, Jr. et al. |
| 2008/0293114 | A1* | 11/2008 | Foody et al. ............... 435/165 |
| 2009/0288788 | A1 | 11/2009 | Castor |
| 2009/0291481 | A1 | 11/2009 | Hillyer |
| 2010/0043782 | A1* | 2/2010 | Kilambi et al. ............ 127/1 |
| 2010/0048884 | A1 | 2/2010 | Kilambi |

FOREIGN PATENT DOCUMENTS

| | | |
|---|---|---|
| CN | 101565725 A | 10/2009 |
| CN | 101584366 A | 11/2009 |
| JP | 2006-263527 | 10/2006 |

OTHER PUBLICATIONS

Puri VP (1983). Explosive Pretreatment of Lignocellulosic Residues with High-Pressure Carbon Dioxide for the Production of Fermentation Substrates. Biotechnology and Bioengineering, v25, p. 3149-3161.*
Palmqvist E et al. (1999). Main and interaction effects of acetic acid, furfural,and p-hydroxybenzoic acid on growth and ethanol productivity of yeasts. Biotechol. Bioeng., v63, p. 46-55.*
Toews KL et al (1995). pH-defining equilibrium between water and supercritical CO2. Influence of SFE of organics and metal chelates. Anal. Chem., v67, p. 4040-4043.*
Dodds DR et al. (2007). Chemicals from Biomass. Science, v318, p. 1250-1251.*
Elliott DC (2001 ).Biomass, Chemicals from. Encyclopedia of Energy, v1, p. 163-174.*
Bobleter O. et al., "Hydrothermal Degradation of Polymers Derived from Plants", *Prog. Polym. Sci.* 19:797-841 (1994).
Kim K.H. et al., "Supercritical $CO_2$ Pretreatment of Lignocellulose Enhances Enzymatic Cellulose Hydrolysis", *Bioresource Technology* 77:139-144 (2001).
Luterbacher J.S. et al., "High-Solids Biphasic $CO_2$—$H_2O$ Pretreatment of Lignocellulosic Biomass", *Biotechnology and Bioengineering* 107(3):451-460 (Oct. 15, 2010).
McWilliams R.C. et al., "Comparison of Aspen Wood Hydrolysates Produced by Pretreatment With Liquid Hot Water and Carbonic Acid", *Applied Biochemistry and Biotechnology* 98-100:109-121(2002).
Mosier N. et al., "Features of Promising Technologies for Pretreatment of Lignocellulosic Biomass", *Bioresource Technology* 96:673-686 (2005).
Park C.Y. et al., "Kinetics and Rate of Enzymatic Hydrolysis of Cellulose in Supercritical Carbon Dioxide", *Korean J. Chem. Eng.*, 18(4):475-478 (2001).
Pasquini D. et al., "Extraction of Lignin from Sugar Cane Bagasse and *Pinus taeda* Wood Chips Using Ethanol-Water Mixtures and Carbon Dioxide at High Pressures", *The Journal of Supercritical Fluids* 36:31-39 (2005).
Peterson A.A. et al., "Thermochemical Biofuel Production in Hydrothermal Media: A Review of Sub-and Supercritical Water Technologies", *Energy & Environmental Science* 1:32-65 (2008).

(Continued)

*Primary Examiner* — Scott Long
*Assistant Examiner* — Sean C Barron
(74) *Attorney, Agent, or Firm* — Scully Scott Murphy & Presser

(57) ABSTRACT

A process for pretreatment of a biomass material, comprising subjecting a biomass material to a biphasic mixture of water and supercritical $CO_2$ at a temperature in the range of 150° C. to 250° C. under high pressure for a time of from 10 seconds to 100 minutes. In particular embodiments, the process is performed as a two-stage temperature process wherein an initial short high-temperature stage is conducted at a temperature of at least 200° C. for up to 20 minutes and a subsequent longer low-temperature stage is conducted at a temperature of at least 140° C. and up to 190° C. for 10-120 minutes.

26 Claims, 14 Drawing Sheets

(56) References Cited

OTHER PUBLICATIONS

Taherzadeh M.J. et al., "Pretreatment of Lignocellulosic Wastes to Improve Ethanol and Biogas Production: A Review", *International Journal of Molecular Sciences* 9:1621-1651(2008).

van Walsum G.P. et al., "Carbonic Acid Enhancement of Hydrolysis in Aqueous Pretreatment of Corn Stover", *Bioresource Technology* 93:217-226 (2004).

Wyman C.E. et al., "Comparative Sugar Recovery and Fermentation Data Following Pretreatment of Poplar Wood by Leading Technologies", *American Institute of Chemical Engineers Biotechnol. Prog.* 25:333-339 (2009).

Wyman C.E. et al., "Comparative Sugar Recovery Data from Laboratory Scale Application of Leading Pretreatment Technologies to Corn Stover", *Bioresource Technology* 96:2026-2032 (2005).

Wyman C.E. et al., "Coordinated Development of Leading Biomass Pretreatment Technologies", *Bioresource Technology* 96:1959-1966 (2005).

Zheng Y. et al., "Supercritical Carbon Dioxide Explosion as a Pretreatment for Cellulose Hydrolysis", *Biotechnology Letters* 17(8):845-850 (Aug. 1995).

Chinese Rejection Decision dated Feb. 16, 2015 received from Application No. 201180027126.2, together with an English-language translation.

Chinese Office Action dated Aug. 1, 2014 received from related Application No. 201180027126.2, together with an English-language translation.

Lloyd, T.A. et al., "Combined sugar yields for dilute sulfuric acid pretreatment of corn stover followed by enzymatic hydrolysis of the remaining solids", Bioresource Technology 96, (2005), pp. 1967-1977.

Luterbacher, J.S. et al., "Two-Temperature Stage Biphasic $CO_2$—$H_2O$ Pretreatment of Lignocellulosic Biomass at High Solid Loadings", Biotechnology and Bioengineering, (Jun. 2012) vol. 109, No. 6, pp. 1499-1507.

Neureiter, M. et al., "Dilute-Acid Hydrolysis of Sugarcane Bagasse at Varying Conditions", Applied Biochemistry and Biotechnology, (2002), vols. 98-100, pp. 49-58.

Oefner, P.J. et al., "Quantitative Studies on Furfural and Organic Acid Formation during Hydrothermal, Acidic and Alkaline Degredation of D-Xylose", Monatshefte fur Chemie, (1992), pp. 547-556.

\* cited by examiner

BIPHASIC SUPERCRITICAL CARBON DIOXIDE-WATER PRETREATMENT OF LIGNOCELLULOSIC BIOMASS

CROSS-REFERENCE TO RELATED APPLICATIONS

This application is a §371 national phase of PCT Application PCT/US2011/027854, filed on Mar. 10, 2011, which claims priority to U.S. Provisional Application No. 61/319,086, filed on Mar. 30, 2010, the contents of each of which are incorporated herein by reference.

This invention was made with government support under Contract No. DT0S59-07-G-00052 awarded by the U.S. Department of Transportation. The government has certain rights in the invention.

FIELD OF THE INVENTION

The present invention relates generally to the conversion of biomass to useful products (e.g., monosaccharides and fuel materials derived therefrom), and more particularly, to the pretreatment step in the processing of biomass.

BACKGROUND OF THE INVENTION

With increases in worldwide energy consumption, economic and environmental issues linked to fossil fuel extraction and use are becoming more pressing. Concerns surrounding the security of global crude oil supplies and of global warming, in particular, have drawn attention to carbon fuels produced from biomass. In the long term, with oil resources becoming more expensive to develop, the chemical industry will need new sources for carbon-based raw materials, which could be provided by biomass.

One of the most specific and versatile routes to produce fuels or other bio-products is to obtain monosaccharides from biomass. These monosaccharides can be converted to fuels or bioproducts by, for example, fermentation (Dodds D R. et al., Science 318:1250-1251, (2007)) or catalytic processes (Huber G. et al., Science 308:1446-1450 (2005); Romén-Leshkov Y. et al., Nature 447:982-985 (2007)). However, selectively producing sugars from lignocellulosic biomass is challenging and typically involves several stages. The initial or "pretreatment" stage consists of partially extracting the hemicellulose and/or lignin fraction of biomass. Pretreatment increases access to catalytic sites for cellulase and xylanase enzymes, which are added during the second (i.e., hydrolysis) stage to depolymerize cellulose and any remaining hemicellulose. In the pretreatment process, care needs to be taken to minimize the degradation of hemicellulose, which is a polymer of mostly pentose and some hexose sugars.

Various pretreatment approaches have included using acid or base solutions or simply pure water (often at higher temperatures) to deconstruct hemicellulose and lignin (Mosier N. et al., Bioresource Technology 96:673-686 (2005)); Wyman C. et al., Bioresource Technology 96:2026-2032 (2005); Wyman C. et al., Bioresource Technology 96:1959-1966 (2005); Wyman C. et al., Biotechnology Progress 25:333-339 (2009)). Some of these technologies involve either flowing the reacting media through the biomass (Gupta R. et al., Biotechnology Progress 25 (2009); Liu C. et al., Applied Biochemistry and Biotechnology 113:977-987 (2004) or an explosive decompression of the total mixture in the case of steam explosion (Bura R. et al., Biotechnology Progress 25:315-322 (2009)) or ammonia fiber explosion (AFEX) (Balan V. et al., Biotechnology Progress 25:365-375 (2009); Teymouri F. et al., Bioresource Technology 96:2014-2018 (2005)). The chemically catalyzed systems are generally environmentally unfriendly and costly, while hot water systems suffer from mass-transfer and dilution issues while demanding significant amounts of energy. These problems have been addressed by, for example, recycling the chemical catalysts or developing packed bed biomass reactors to increase mixing. However, these processes still generally suffer from a high degree of complexity, high cost, low sugar yields (i.e., low efficiencies), and significant production of undesired byproduct, such as those based on furfural.

Moreover, the biomass conversion processes currently in use generally suffer from a significant lack in versatility in being able to process a wide range of different biomass materials under substantially the same conditions with the same equipment. On the contrary, conventional practice generally requires the use of significantly different equipment and/or processing conditions for processing different types of biomass (e.g., hardwood vs. perennial grasses). This significant limitation in current biomass conversion technologies presents a major hindrance in making biomass-to-energy technology competitive with conventional energy production and usage. The ability to apply a single process for any of a wide variety, or mixture, of biomass materials provides the significant advantage of producing useful materials and energy from any biomass that may become available, whether it be indigenous or non-indigenous to the area in which the biomass conversion facility is located.

SUMMARY OF THE INVENTION

The present invention provides an environmentally friendly method for pretreating any of a variety of biomass materials and mixtures thereof. The method renders the biomass material significantly more susceptible to a subsequent hydrolysis operation, thereby advantageously raising sugar yields. Temperatures, pressures, processing time, and relative amounts of carbon dioxide and water are carefully selected to maximize sugar yields in a subsequent hydrolysis operation while minimizing unwanted byproducts.

The environmentally friendly nature of the method lies primarily in the use of a mixture of supercritical carbon dioxide and water at elevated temperatures and pressures. Solvents, acids, and bases, as well as other costly and environmentally deleterious materials, are not required for the method. Carbon dioxide is non-toxic and can be almost completely recycled. Moreover, any losses can be largely compensated by the $CO_2$ generated during a subsequent fermentation.

A particular advantage of the instant pretreatment process is its versatility in being able to process a wide range of different biomass materials under substantially the same conditions with the same equipment. This ability is to be sharply contrasted with conventional technologies that generally require significantly different equipment and processing conditions for processing different types of biomass. The ability of the instant pretreatment process to efficiently process any of a wide variety, or mixture, of biomass materials provides the significant advantage of producing useful materials and energy from any biomass that may be available, whether native or non-native to the location in which the biomass processing facility is located.

Another significant advantage of the instant pretreatment process is its ability to be integrated with a subsequent hydrolysis process in a continuous configuration or mode (i.e., by using the same equipment without the need for transferring the pretreated biomass between multiple pretreatment units or to a separate hydrolysis unit). In an industrial setting the instant pretreatment process can take the form of a continuous tubular reactor, as opposed to non-continuous processes with multiple stages and downtime, which are generally higher in capital and have higher operating costs.

Yet another significant advantage of the instant pretreatment process is its ability to operate at high solid contents. For example, the instant process shows competitive yields with at least a 40 wt % solid content. High solid content during pretreatment will determine how much water is carried through the process, which ultimately has to be separated from the resulting product. In general, the higher the solid content, the higher the energy efficiency of the process.

In particular embodiments, the process includes subjecting a biomass material to a biphasic mixture of water and supercritical $CO_2$ at a temperature in the range of 150° C. to 250° C. under high pressure for a time of 10 seconds to 100 minutes. In some embodiments, the pressure is preferably in the range of 150-225 bar or 190-210 bar. In other embodiments, the temperature is preferably in the range of 155-200° C. or 160-170° C. In particular embodiments, the processing time is about 60 minutes. In other particular embodiments, the biphasic mixture is formed by first mixing the biomass material with water to obtain a slurry having a moisture content of at least 10% and not more than 85%, and providing liquid $CO_2$ (and possibly additional water) to the slurry in a closed reactor.

In yet other embodiments, the pretreatment process described herein is conducted as a two-stage temperature process wherein an initial short high-temperature stage is followed by a subsequent longer low-temperature stage. The instant two-stage process is a significant improvement over the art for at least the reason that it provides a shortened pretreatment process while minimizing byproduct formation, while at the same time being environmentally friendly and cost effective. In particular embodiments, the two-stage process includes an initial short high-temperature stage conducted at a temperature of at least 200° C. for 1-20 minutes and a subsequent longer low-temperature stage conducted at a temperature of up to 180° C. for 40-100 minutes.

Part 1 shows glucan to glucose yields. Part 2 shows xylan, arabinan and mannan to xylose, arabinose and mannose yields. Part 3 shows degradation product yields (xylan and arabinan to furfural and glucan and mannan to 5-HMF).

Figure 10:
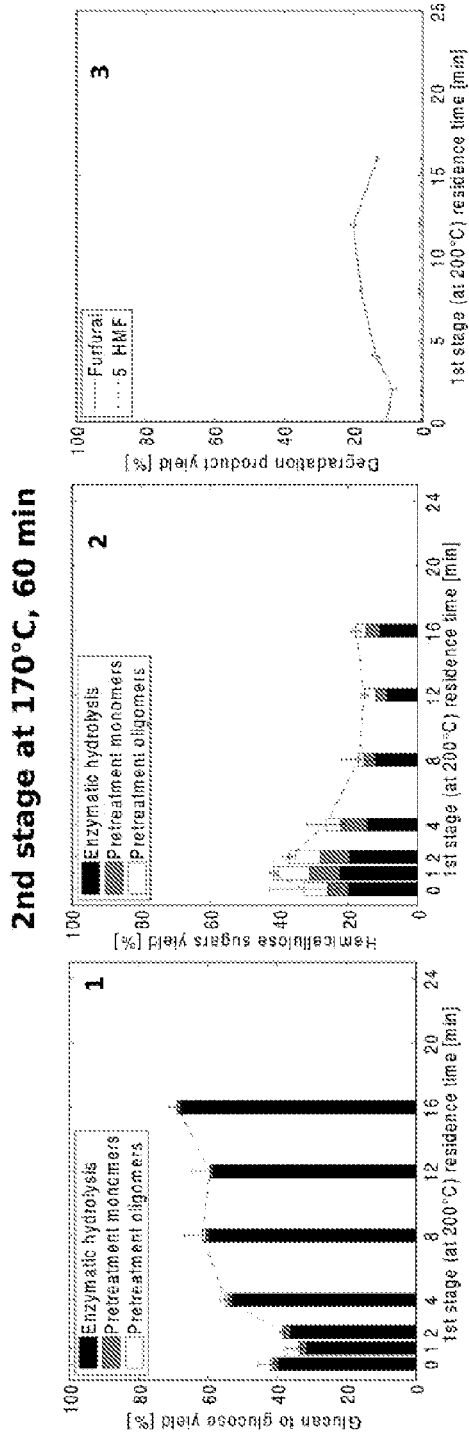

FIG. 10 (parts 1-3). Charts showing yields for two-temperature stage pretreatment of 40 wt % solids (water biomass mixture) large-particle mixed hardwood. All yields were obtained after pretreatment at 200 bar, 200° C. for a varying residence time and 170° C. for 60 minutes followed by 72 hours of enzymatic hydrolysis (15 FPU/gr glucan). Part 1 shows glucan to glucose yields. Part 2 shows xylan, arabinan and mannan to xylose, arabinose and mannose yields. Part 3 shows degradation product yields (xylan and arabinan to furfural and glucan and mannan to 5-HMF).

Figure 11:
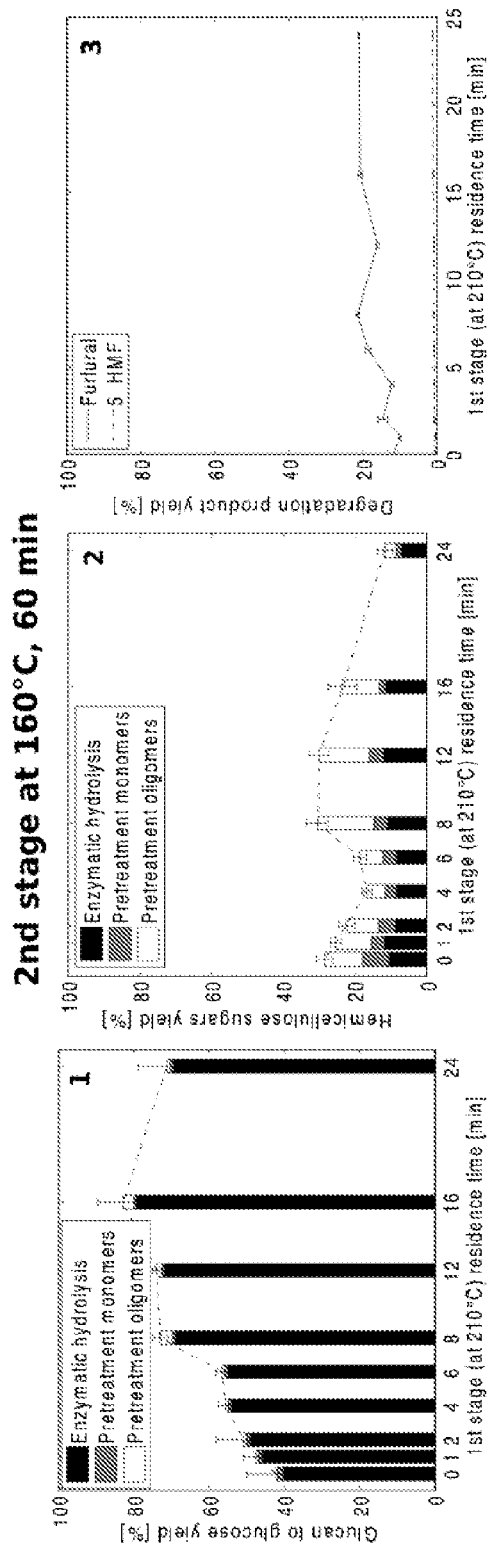

FIG. 11 (parts 1-3). Charts showing yields for two-temperature stage pretreatment of 40 wt % solids (water biomass mixture) large-particle mixed hardwood. All yields were obtained after pretreatment at 200 bar, 210° C. for a varying residence time, and 160° C. for 60 minutes followed by 72 hours of enzymatic hydrolysis (15 FPU/gr glucan). Part 1 shows glucan to glucose yields. Part 2 shows xylan, arabinan and mannan to xylose, arabinose and mannose yields. Part 3 shows degradation product yields (xylan and arabinan to furfural and glucan and mannan to 5-HMF).

Figure 12:
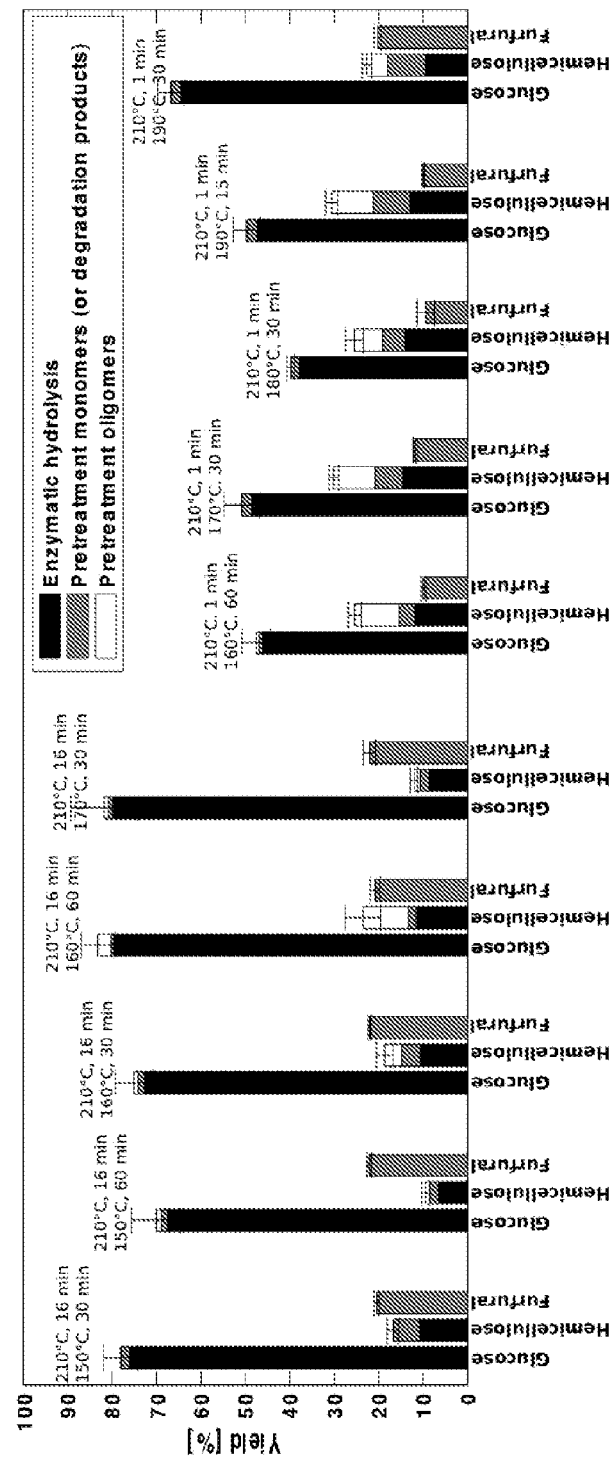

FIG. 12. Charts showing yields for two-temperature stage pretreatment of 40 wt % solids (water biomass mixture) large particle mixed hardwood. All yields were obtained after pretreatment at 200 bar and 72 hours of enzymatic hydrolysis (15 FPU/gr glucan). Pretreatment conditions are indicated above each set of yields. Bars represent glucan to glucose yields (indicated by "glucose"); xylan, arabinan and mannan to xylose, arabinose and mannose yields (indicated by "hemicellulose"); and xylan and arabinan to furfural yields indicated by "furfural").

Figure 13:
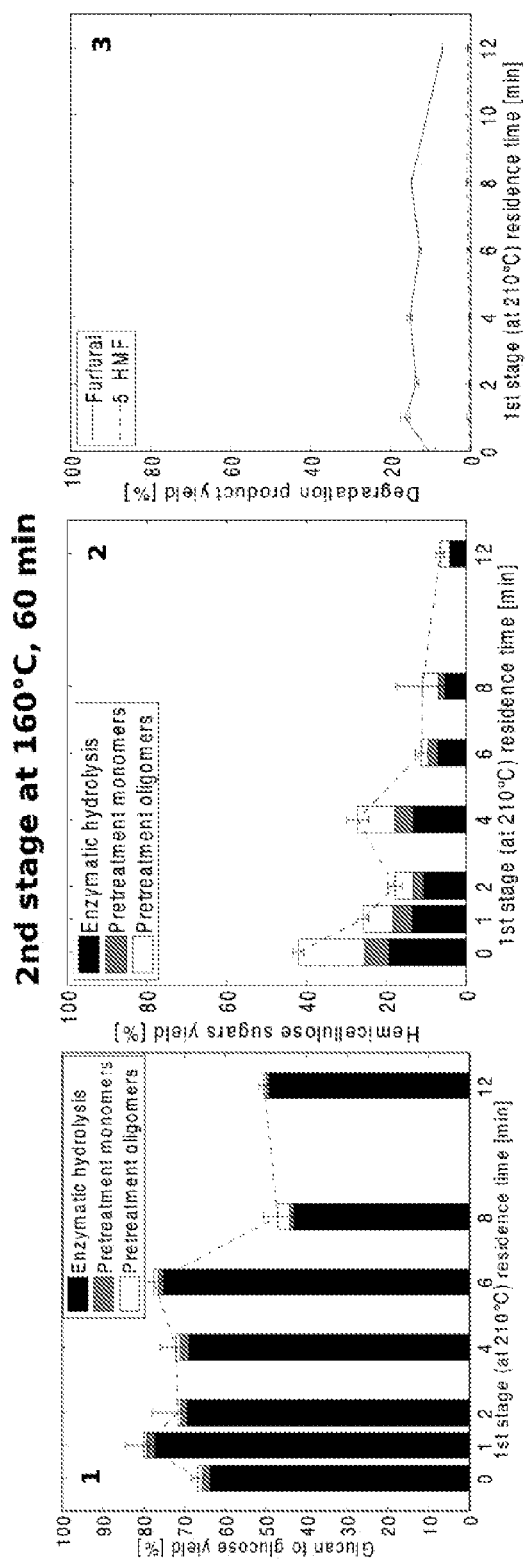

FIG. 13 (parts 1-3). Charts showing yields for two-temperature stage pretreatment of 40 wt % solids (water biomass mixture) large-particle switchgrass. All yields were obtained after pretreatment at 200 bar, 210° C. for a varying residence time, and 160° C. for 60 minutes followed by 72 hours of enzymatic hydrolysis (15 FPU/gr glucan). Part 1 shows glucan to glucose yields. Part 2 shows xylan, arabinan and mannan to xylose, arabinose and mannose yields. Part 3 shows degradation product yields (xylan and arabinan to furfural and glucan and mannan to 5-HMF).

Figure 14:
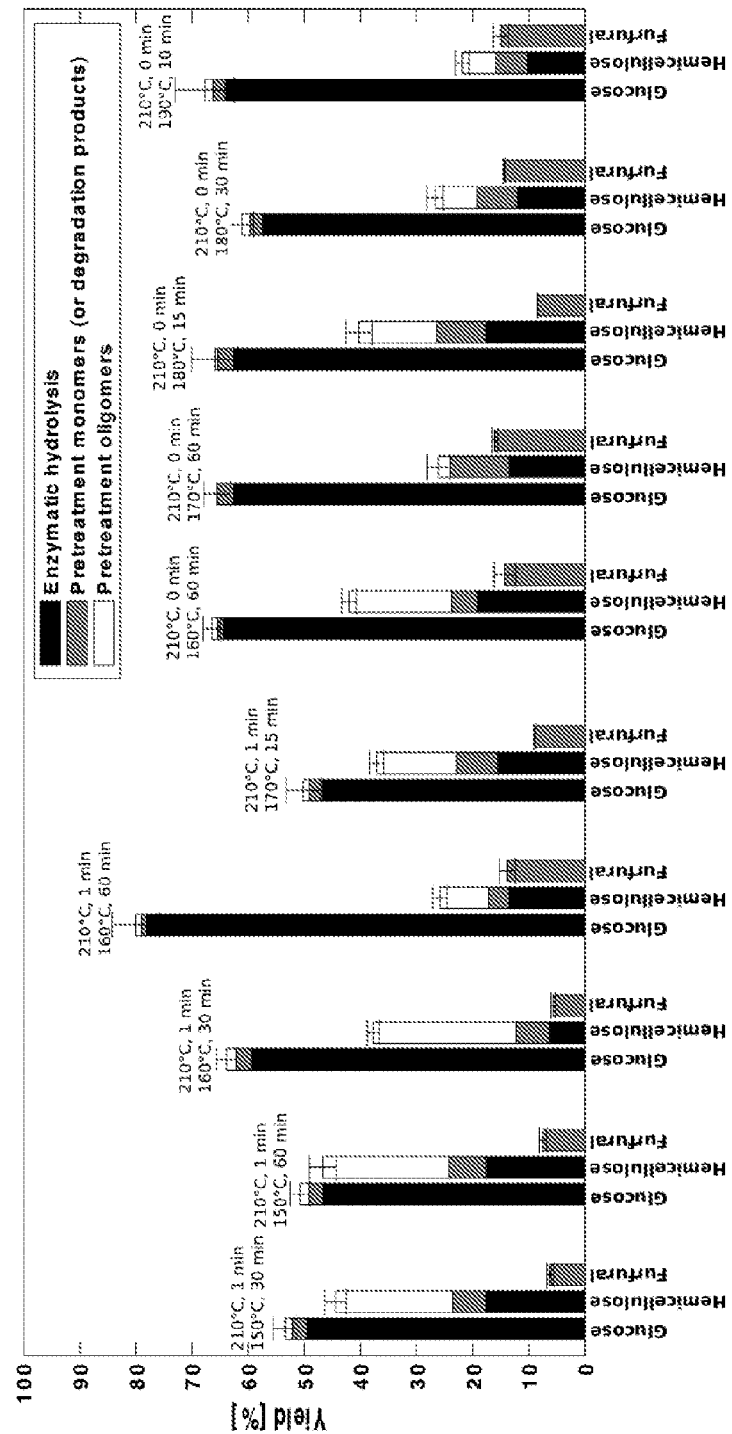

FIG. 14. Charts showing yields for two-temperature stage pretreatment of 40 wt % solids (water biomass mixture) large particle switchgrass. All yields were obtained after pretreatment at 200 bar and 72 hours of enzymatic hydrolysis (15 FPU/gr glucan) Pretreatment conditions are indicated above each set of yields. Bars represent glucan to glucose yields (indicated by "glucose"); xylan, arabinan and mannan to xylose, arabinose and mannose yields (indicated by "hemicellulose"); and xylan and arabinan to furfural yields indicated by "furfural").

DETAILED DESCRIPTION OF THE INVENTION

As used herein, the term "about" generally indicates within ±0.5%, 1%, or up to ±2% of the indicated value. For example, a temperature of about 150° C. generally indicates, in its broadest sense, 150° C.±2% (i.e., 150° C.±3° C., or 147-153° C.). In addition, the term "about" can indicate either a measurement error (i.e., by limitations in the measurement method), or alternatively, a variation or average in a physical characteristic of a group (e.g., a level of variation in a compositional characteristic).

In accordance with the present invention, a biphasic mixture of supercritical carbon dioxide (i.e., SC—$CO_2$) and water is used as a pretreatment medium. As understood in the art, and as used herein, the term "supercritical carbon dioxide" refers to the phase of carbon dioxide at or above its critical temperature ($T_a$) and at or above its critical pressure ($P_c$). The critical temperature of carbon dioxide is about 31.1° C. The critical pressure of carbon dioxide is about 73.9 bar (72.9 atm or 1,072 psig). As known in the art, in the supercritical phase, carbon dioxide possesses characteristics of both a liquid and a gas. This dual nature advantageously endows SC—$CO_2$ with the properties of a low-viscosity fluid (i.e., low surface tension solvent) and the penetrating properties of a gas. In the instant process, these dual properties significantly improve the efficacy of the pretreatment process in separating the cellulose component from hemicellulose and lignin components. It has further been found herein that the particular biphasic mixture described herein dramatically improves the pretreatment process.

The biphasic mixture of SC—$CO_2$ and water includes i) a supercritical phase composed predominantly of carbon dioxide and some water, and ii) a liquid phase composed mostly of water with some carbon dioxide to form a carbonic acid solution. The supercritical phase may contain precisely, at least, up to, or less than, for example, 10%, 15%, 20%, 25%, 30%, 35%, 40%, 45%, or 50% water, or an amount of water in a range bounded by any two of these values (wherein % is understood to mean mol %). In some embodiments, the supercritical phase of $CO_2$ is saturated with water, wherein it is understood that the amount of water (in %) required for saturation is highly dependent on the temperature and pressure. The liquid aqueous phase may contain precisely, at least, up to, or less than, for example, 0.1%, 0.2%, 0.5%, 1%, 1.5%, 2%, 2.5%, or 3% $CO_2$, or an amount of $CO_2$ in a range bounded by any two of these values.

The temperature used in the instant pretreatment process is preferably in the range of about 150° C. and 250° C. In different embodiments, the temperature is within a range bounded by any two of the following temperatures: 150° C., 155° C., 160° C., 165° C., 170° C., 175° C., 180° C., 185° C., 190° C., 195° C., 200° C., 205° C., 210° C., 215° C., 220° C., 225° C., 230° C., 235° C., 240° C., 245° C., and 250° C. In different embodiments, the temperature used in the instant pretreatment process is preferably in the range of 155° C.-250° C., 160° C.-250° C., 165° C.-250° C., 170° C.-250° C., 180° C.-250° C., 190° C.-250° C., 200° C.-250° C., 155° C.-225° C., 160° C.-225° C., 165° C.-225° C., 170° C.-225° C., 180° C.-225° C., 190° C.-225° C., 200° C.-225° C., 155° C.-200° C., 160° C.-200° C., 165° C.-200° C., 170° C.-200° C., 180° C.-200° C., 190° C.-200° C., 155° C.-180° C., 160° C.-180° C., 165° C.-180° C., 170° C.-180° C., 155° C.-175° C., 160° C.-175° C., 165° C.-175° C., 170° C.-175° C., 155° C.-170° C., 160° C.-170° C., 165° C.-170° C., 155° C.-165° C., and 160° C.-165° C.

The pressure used in the instant pretreatment process is preferably at least the critical pressure of carbon dioxide, i.e., at least 74 bar. Such a pressure is referred to herein as a "high" or "elevated" pressure. In different embodiments, the pressure is precisely, about, or at least, for example, 80 bar, 90 bar, 100 bar, 110 bar, 120 bar, 130 bar, 140 bar, 150 bar, 160 bar, 170 bar, 180 bar, 190 bar, 200 bar, 205 bar, 210 bar, 215 bar, 220 bar, 225 bar, 230 bar, 235 bar, 240 bar, 245 bar, 250 bar, 260 bar, 270 bar, 280 bar, 290 bar, or 300 bar, or a pressure within a range bounded by any two of the foregoing exemplary pressures. In different embodiments, the pressure is preferably in the range of 150-250 bar, 150-225 bar, 150-210 bar, 150-200 bar, 150-190 bar, 150-

180 bar, 160-250 bar, 160-225 bar, 160-210 bar, 160-200 bar, 160-190 bar, 160-180 bar, 170-250 bar, 170-225 bar, 170-210 bar, 170-200 bar, 170-190 bar, 170-180 bar, 180-250 bar, 180-225 bar, 180-210 bar, 180-200 bar, 180-190 bar, 190-250 bar, 190-225 bar, 190-210 bar, 190-200 bar, 200-300 bar, 200-250 bar, 200-225 bar, 200-210 bar, 210-300 bar, 210-250 bar, 210-225 bar, 210-220 bar, 225-300 bar, 225-250 bar, and 250-300 bar.

The period of time that the biomass is processed (i.e., "processing time") with the above-described biphasic mixture is generally at least 10 seconds, 20 seconds, 30 seconds, or 1 minute, and generally up to 40, 60, 80, or 100 minutes. In different embodiments, the processing time may be preferably be in a range bounded by any two of the following times: 10 seconds, 20 seconds, 30 seconds, 1 minute, 2 minutes, 5 minutes, 10 minutes, 15 minutes, 20 minutes, 30 minutes, 40 minutes, 50 minutes, 60 minutes, 70 minutes, 80 minutes, 90 minutes, and 100 minutes.

The biomass can be any of the biomass materials known in the art. As used herein, the term "biomass" is generally defined as any natural-derived material having a cellulosic component. Generally, the biomass material contains at least one component selected from cellulosic, hemicellulosic, and lignin components, as commonly found in wood and other lignocellulosic plant materials. Typically, the biomass materials considered herein include all three components of cellulose (β-1,4-glucan), hemicellulose, and lignin. Generally, the biomass considered herein is not useful as a food source, nor is it food waste.

Depending on the biomass material, the amount of cellulose may account for at least, about, or up to, for example, 30, 35, 40, 45, 50, 55, or 60% of the biomass material; the amount of hemicellulose may account for at least, about, or up to, for example, 10, 15, 20, 25, 30, 35, 40, or 45% of the biomass material; and, the amount of lignin may account for at least, about, or up to, for example, 5, 10, 15, 20, 25 or 30% of the biomass material. The biomass material may also contain an amount of cellulose, hemicellulose, and lignin within ranges of the exemplary amounts provided above. The biomass material can be further characterized by, for example, the amount of particular polysaccharides from which cellulose and/or hemicellulose are constructed. As known in the art, cellulose is composed almost exclusively of polymers of glucose (i.e., glucan), while hemicellulose includes several additional polysaccharides, including xylan, mannan, and arabinan. In some embodiments, the biomass material includes xylan in an amount of precisely, about, at least, less than, or up to, for example, 5, 10, 15, 20, 25, or 30 wt %, or within a range bounded by any two of these values. In other embodiments, the biomass material includes mannan in an amount of precisely, about, at least, less than, or up to, for example, 0, 0.1, 0.2, 0.3, 0.4, 0.5, 0.6, 0.7, 0.8, 0.9, 1, 1.2, 1.5, 1.7, 2, 2.5, 3, 3.5, 4, 4.5, or 5 wt %, or within a range bounded by any two of these values. In other embodiments, the biomass material includes arabinan in an amount, of precisely, about, at least, less than, or up to, for example, 0, 0.1, 0.2, 0.3, 0.4, 0.5, 0.6, 0.7, 0.8, 0.9, 1, 1.2, 1.5, 1.7, 2, 2.5, 3, 3.5, 4, 4.5, or 5 wt %, or within a range bounded by any two of these values. The composition of the biomass material may be categorized by other suitable standards, e.g., elemental analysis and identification of trace elements. The amount of protein or nitrogen content are other compositional qualities that may be used to characterize the biomass material. The protein content may be, for example, about, up to, or less than, for example, 1, 2, 5, 10, 15, 20, or 25%.

The biomass material can be, for example, wood (e.g., hardwood and softwood), a grass or mixture thereof (e.g., perennial grass or cereal grass), sugarcane (e.g., sugarcane bagasse), paper, cardboard, and hull material (e.g., grain hulls or nut hulls). Some particular types of woods considered herein include poplar, pine, aspen, cedar, willow, birch, maple, oak, spruce, and bamboo. Some examples of perennial grasses include switchgrass (i.e., *Panicum virgatum*), big bluestem, miscanthus, alfalfa, orchard grass, and reed canarygrass. Some examples of cereal grasses include wheat, rye, oat, barley, soy, and hemp, as well as straws derived therefrom. A particular example of hull material is corn stover, which generally includes at least one of the leaves, husks, stalks, or cobs of corn plants.

As known in the art, there is no uniform lignin composition found in nature. Lignin is a random polymer that shows significant compositional variation between plant species. Furthermore, many other conditions, such as environmental conditions and age influence the lignin content of plants. Lignins differ mainly in the ratio of the three alcohol units. Softwood lignins are composed of approximately 80 wt % coniferyl, 14 wt % p-coumaryl, and 6 wt % sinapyl alcohol units. Hardwood lignins are composed of approximately 56 wt % coniferyl, 4 wt % p-coumaryl and 40 wt % sinapyl alcohol units. Grass lignins are rich in p-coumaryl units. The polymerization of p-coumaryl alcohol, coniferyl alcohol, and sinapyl alcohol forms the p-hydroxyphenyl (H), guaiacyl (G) and syringyl (S) components of the lignin polymer, respectively. In different embodiments, the lignin of the biomass material contains about, at least, up to, or less than, for example, 20 wt %, 30 wt %, 40 wt %, 50 wt %, 60 wt %, 70 wt %, 80 wt %, or 90 wt % coniferyl alcohol units; about, at least, up to, or less than, for example, 1 wt %, 2 wt %, 3 wt %, 4 wt %, 5 wt %, 10 wt %, 20 wt %, 30 wt %, 40 wt %, 50 wt %, 60 wt %, 70 wt %, 80 wt %, or 90 wt % p-coumaryl alcohol units; and about, at least, up to, or less than, for example, 1 wt %, 2 wt %, 3 wt %, 4 wt %, 5 wt %, 6 wt %, 7 wt %, 8 wt %, 9 wt %, 10 wt %, 15 wt %, 20 wt %, 30 wt %, 40 wt %, 50 wt %, 60 wt %, or 70 wt % sinapyl alcohol units.

In some embodiments, the biomass material undergoing the pretreatment process is a single type of biomass material. By being a single type of biomass material, the biomass material is completely or substantially uniform in its compositional characteristics, i.e., the biomass material shows very little or no variation in compositional characteristics between pieces of biomass material to be processed. Various compositional characteristics have been described above, which can be used in determining the homogeneity or heterogeneity of a biomass source. Generally, biomass originating from the same type of plant (e.g., switchgrass) or a particular species or variety thereof constitutes a single type of biomass. Variation in the composition between different parts of the plant is common, e.g., between leaves and stem, and this compositional variation is generally not considered a mixture of biomass, although there may be advantages in some embodiments for separating different components of a plant source and selectively processing one or more parts of the plant.

In other embodiments, the biomass material is a mixture of biomass materials. Any combination of biomass materials is considered herein. The mixture can be, for example, a mixture of hardwood and softwood, or wood and perennial grass, or a variety of perennial grasses, or variety of woods, or a variety of hull materials, or wood and cereal grass, or grass and paper, or wood and hull material, or a more variegated mix of such materials.

Any one or more of the classes or particular types of biomass materials described above may also be excluded from the pretreatment method described herein. In certain embodiments, aspen wood and/or southern yellow pine are excluded from the biomass materials used.

The biomass is generally charged into a high pressure vessel (reactor) suitable for introducing carbon dioxide therein and pressurizing the carbon dioxide to form a supercritical phase thereof along with water. The design and construction of such vessels are well known in the art. In particular embodiments; the pretreatment process employing the biphasic mixture described above is practiced by first mixing the biomass material with water to obtain a slurry or wetted (i.e., moisturized) biomass material having a moisture content of precisely, about, at least, or no more than 3%, 4%, 5%, 8%, or 10%, and up to 60%, 70%, 75%, 80%, or 85%. Liquefied or supercritical $CO_2$ is then introduced into the vessel holding the wetted biomass material, and thereafter, the $CO_2$ is pressurized and heated with the wetted biomass to form the biphasic SC—$CO_2$— water mixture described above.

In alternate embodiments, supplemental water could be introduced into the vessel along with liquefied or supercritical $CO_2$. In this case, $CO_2$ would typically be in the supercritical state and water would be in a pressurized subcritical liquid state. In particular embodiments, a biphasic mixture is formed by injecting a mixture of water and carbon dioxide into a reactor containing the biomass material, wherein the biomass, before being contacted with the mixture of carbon dioxide and water, is substantially dry by having a moisture content of no more than or less than 10%, 9%, 8%, 7%, 6%, or 5%. In other embodiments, a biphasic mixture is formed by injecting a mixture of water and carbon dioxide into a reactor containing the biomass material, wherein the biomass, before being contacted with the mixture of carbon dioxide and water, is dryer than it will be after the water and $CO_2$ injection when the final mixture is achieved by having a moisture content of no more than or less than 60%, 50%, 40%, 30%, 20%, 10%, or 5%. For example, biomass from a field can have as much as 50-60% moisture, so one could inject some water with the $CO_2$ to bring the moisture up from 50% to 60%. Alternatively, one may be provided with biomass having 10%-15% moisture (typical for field dried biomass), bring the moisture content to 20%, and inject the remainder of the water with the $CO_2$ to get to 60% moisture.

The pretreatment process can use any suitable moisture content. In different embodiments, the moisture content of the biomass is precisely, about, at least, up to, or less than, for example, 3, 4, 5, 10, 15, 20, 25, 30, 35, 40, 45, 50, 55, 65, 70, 75, 80, and 85%. In some embodiments, the moisture content is within a range bounded by any two of the foregoing exemplary moisture levels.

In some embodiments, alcohols are excluded from the pretreatment process described herein. In other embodiments, one or more of any of a variety of organic solvents (e.g., alcohols, ketones, ethers, and the like), or all organic solvents, are excluded from the pretreatment process described herein. In yet other embodiments, a strong mineral acid (e.g., sulfuric acid, nitric acid, or hydrochloric acid) and/or a base (e.g., sodium hydroxide) are excluded from the pretreatment process described herein. In particular embodiments, the pretreatment process employs solely biomass material, carbon dioxide, and water.

The solids content (i.e., "solids loading" or "biomass loading") used in the pretreatment process is preferably at least 20 wt %. The solids loading refers to the amount of biomass being processed at the start of the process relative to the total weight of biomass and process water. Some biomass loading values include precisely, about, or at least, for example, 20, 25, 30, 35, 40, 45, or 50 wt %, or a loading value within a range thereof.

In particular embodiments, the pretreatment process described above is performed as a two-stage temperature process wherein an initial short high-temperature stage (i.e., at least or above 200° C.) is followed by a subsequent longer low-temperature stage (i.e., less than 200° C.). The temperature and time for the initial short high-temperature stage are selected in order to provide an initial high rate of separation of cellulose from lignin and hemicellulose materials. Although sustained processing at the high temperature would significantly hasten the cellulose separation process, prolonged processing at such a high temperature would have the significant negative effect of substantially increasing the rate of byproduct formation and destroying the valuable hemicellulose fraction. For this reason, a subsequent longer low-temperature stage is employed in order to continue the separation process while minimizing byproduct formation by virtue of the lower temperature. The combination of the two temperature stages advantageously overcomes a significant problem encountered in the art in which one skilled in the art had the choice of either a longer processing time with minimized byproduct formation or a shorter processing time with a significantly increased amount of byproduct formation. The instant two-stage process is a significant improvement over the art for at least the reason that it provides a shortened pretreatment process while minimizing byproduct formation, while at the same time being environmentally friendly and cost effective by virtue of the supercritical carbon dioxide biphasic mixture described herein.

In particular embodiments, the two-stage process includes an initial short high-temperature stage conducted at a temperature of precisely, about, or at least 200° C. for up to or less than 20 minutes and a subsequent longer low-temperature stage conducted at a temperature of at least 140° C. and up to or less than 170° C., 180° C., or 190° C. for 10-120 minutes, 30-120 minutes, or 40-120 minutes. It is understood that processing times are selected from the above exemplary ranges that make the high-temperature stage shorter in duration than the low-temperature stage. In different embodiments, the temperature used in the initial short high-temperature stage is precisely, about, or at least, for example, 200° C., 210° C., 215° C., 220° C., 225° C., 230° C., 235° C., 240° C., 245° C., or 250° C., or a temperature within a range bounded by any two of the foregoing exemplary temperatures. The time at which the high temperature stage is maintained can be precisely, about, up to, or less than, for example, 1, 2, 3, 4, 5, 6, 7, 8, 9, 10, 15, or 20 minutes, wherein, generally, higher temperatures are sustained for shorter times to achieve the same or similar result. In different embodiments, the temperature used in the longer low-temperature stage is precisely, about, up to, or less than, for example, 190° C., 180° C., 175° C., 170° C., 165° C., 160° C., 155° C., 150° C., 145° C., or 140° C., or a temperature within a range bounded by any two of the foregoing exemplary temperatures. The time at which the lower temperature stage is maintained can be precisely or about, for example, 10, 15, 20, 25, 30, 35, 40, 45, 50, 55, 60, 65, 70, 75, 80, 85, 90, 95, 100, 105, 110, 115, or 120 minutes, or a time within a range bounded by any two of these exemplary values.

In the two-stage temperature process, the temperature can be adjusted suddenly or gradually (e.g., by a specified rate of temperature change). For example, the temperature may be increased to precisely, about, or at least 200° C. for up to or less than 20 minutes, and then ramped down at a constant or variable rate (e.g., between 0.1 and 100° C./min) to a lower temperature (as described above). The ramp-down phase could occur during the entire process or until a lower stage temperature is reached. In some embodiments, the high temperature may be reached gradually (from, e.g., room temperature) by a specified rate of temperature change. The subsequent low temperature may then be reached suddenly (e.g., within 30 seconds or 1 minute) or gradually by a specified rate of temperature change. Any of the temperature ramping stages may also be interrupted by one or more plateau stages at which an intermediate temperature is maintained for a period of time.

In the pretreatment process, biomass is generally broken down in size to a particulate level for the biomass to be efficiently processed. The average size of the biomass particles can be any suitable size. In different embodiments, the average size of the biomass particles is about, at least, up to, or less than, for example, 10 cm, 8 cm, 7, cm, 6 cm, 5 cm, 3 cm, 2 cm, 1 cm, 5 mm, 2.5 mm, or 1 mm. The exemplary sizes provided can represent limits for all three dimensions of the biomass particles, or alternatively, be representative of at least one or two dimensions of the biomass particles.

The invention is also directed to processes in which the pretreatment process, described above, is followed by an enzymatic hydrolysis process for converting pretreated biomass into fermentable sugars, which are primarily monosaccharides, such as glucose. In some embodiments, the pretreated biomass is transferred from the high pressure vessel into a hydrolysis unit and processed by any of the conventional hydrolytic technologies and conditions known in the art. As is well-established in the art, the pretreated biomass is generally reacted with a cellulase enzyme to facilitate hydrolysis. In other embodiments, the pretreatment process, described above, is followed by a hydrolysis stage in a continuous manner. By being a "continuous process", the pretreatment and hydrolysis processes use the same equipment without the need for transferring the pretreated biomass to a separate hydrolysis station. For example, the material can be subjected to a drop in pressure and temperature following pretreatment, but continue to be pumped through a continuous tubular setup. This avoids the use of discontinuous unit operations, such as various bath reactors. Indeed, the use of $CO_2$ as a co-solvent for water will allow for the total mixture to be pumped through a tubular pretreatment setup in a much easier manner than would have been the case for the same high-solids mixture without the $CO_2$. Such a continuous setup is able to directly feed into a continuous enzymatic hydrolysis tubular reactor making the entire system continuous.

The pretreatment process described herein dramatically increases cellulose availability and digestibility in the subsequent hydrolysis step. The efficacy of the pretreatment process can, in large part, be characterized by the sugar yield achieved in the subsequent hydrolysis step. Preferably, the pretreatment process described herein results in a sugar yield of at least 50%. In other embodiments, the pretreatment process described herein results in a sugar yield of at least 55%, 60%, 65%, 70%, 75%, or 80%.

In further aspects of the invention, the method further includes converting monosaccharides produced in the hydrolysis step into a useful commodity, most notably ethanol, liquid alkanes biofuel, or carbon-based commodity chemicals (i.e., "biomaterials"). Fermentation and catalytic processes for the production of ethanol, alkane biofuel, and biomaterials are well known in the art. Various carbon based commodity chemicals can be produced from monosacchamides (Dodds D R. et al., Science 318:1250-1251, (2007)). For example, lactic acid, produced by fermentation, can be chemically converted to methyl lactate, lactide, and polylactic acid (PLA). PLA, in particular, may serve as a biodegradable alternative to polyethylene terephtalate (PET). Succinic acid can also be produced from monosaccharides, and could be used in place of maleic anhydride, which is currently produced from butane. Maleic anhydride is used as a starting material for producing polymers and industrial solvents. Catechols and other aromatic alcohols can also be produced from monosaccharides, which could replace current production processes that rely on environmentally unfriendly benzene as a starting material.

Cellulose-derived ethanol and other biofuels are increasingly being viewed as preferred fuel alternatives because of the renewable and ecofriendly sources relied upon in their production. The ecological benefits of such bio-derived fuels are particularly evident when the biomass from which they are produced are the cellulosic parts of plants (e.g., corn stover or hull materials) that are generally non-edible and undesirable byproducts resulting from harvesting of crops. Typically, such cellulosic remnants are either discarded, used as fertilizer, or used as fodder. Thus, by using such unwanted cellulosic byproducts, competition with natural resources and food stores is avoided. Furthermore, since cellulosic byproducts are not specifically produced as a fuel source, they do not require any additional expenditure for their production, and are therefore cheap and plentiful.

In an ethanol fermentation process, free sugars and/or oligosaccharides produced in the hydrolysis step are subjected to fermentation conditions for the production of ethanol. Fermentation processes are well known in the art. Typically, fermentation is accomplished by combining one or more fermenting microorganisms with the produced sugars under conditions suitable for fermentation. The fermenting broth is typically heated, e.g., to 20-40° C. for yeast organisms (such as *Saccharomyces cerevisiae*), or to higher temperatures for thermophilic organisms (such as *Thermoanaerobacter* species). The ethanol is then removed (or partially removed) from the broth, typically by distillation, leaving behind fermentation process water.

A significant problem encountered in hydrolysis and ethanol fermentation processes is the production of inhibitory compounds (e.g., acetate, furfural, ketones, and alcohols, such as hydroxy aromatics) during the pretreatment process. Typically, the inhibitor compounds include at least one or more compounds selected from carboxylic acids (i.e., carboxylates), furfural (i.e., 2-furfural), 5-hydroxymethylfurfural (5-HMF), and phenolic compounds. The carboxylic acid can be, for example, acetic acid (acetate), propanoic acid, or higher acids, or their deprotonated (e.g., salt) forms. The phenolics are typically those resulting from lignin degradation. The phenolics can be, for example, phenol, guaiacol, eugenol, cresols, syringol, 4-hydroxybenzaldehyde (4-HB or HB), vanillin, vanillic acid (VA), homovanillic acid, syringaldehyde, 3,4,5-trimethoxybenzaldehyde, 4-hydroxyacetophenone (4-HAP or HAP), acetovanillone, acetosyringone, 4-hydroxybenzoic acid, syringic acid, 3,4,5-trimethoxyacetophenone, ferulic acid, caffeic acid, sinapyl alcohol, coniferyl alcohol, and p-coumaric acid. Inhibitor compounds have the deleterious effect of inhibiting one or more process steps (e.g., the hydrolysis or fermentation process), thereby causing a decreased level of ethanol pro duction. In particular, acetate is generally produced from hydrolysis of acetylated ferulates associated with the hemicellulose fraction of biomass. Moreover, the accumulation of inhibitor compounds is increased with higher solids loading of biomass.

The pretreatment process described herein preferably minimizes the production of inhibitory compounds. Therefore, the efficacy of the pretreatment process can, in large part, be characterized by the yield of inhibitory compounds. Preferably, the pretreatment process described herein results in a yield of inhibitor compounds (particularly, furfural and/or its derivatives) of no more than, or less than, 30%. In other embodiments, the pretreatment process described herein results in a yield of inhibitor compounds of no more than, or less than, 25%, 20%, 15%, 10%, 5%, 2%, or 1%.

Examples have been set forth below for the purpose of illustration and to describe certain specific embodiments of the invention. However, the scope of this invention is not to be in any way limited by the examples set forth herein.

2009). All species of biomass were dried, and had moisture contents of 7 to 12 wt %. The biomass was size reduced using a cutting mill (IKA®, Wilmington, N.C.) with a 1 mm screen to remove dust-like particles that would be lost during filtering (U.S. Standard 400 sieve, E. H. Sargent and Co., Chicago, Ill.). Before pretreatment, following pretreatment and after washing, biomass moisture content was determined by weighing it before and after its placement in an oven at 105° C. for 12 hour and in a desiccator for 5 hour.

Biomass feedstocks were analyzed for neutral detergent fibers (NDF), acid detergent fibers (ADF), and detergent lignin (Lignin). All these analyses were performed by Dairy One® (Ithaca, N.Y.) using methods described by Van Soest P J et al. (Van Soest P J et al., J. Dairy Sci. 74:3583-3597 (1991)). Biomass feedstocks were further analyzed for glucan, xylan, arabinan, and mannan using the protocol developed by the National Renewable Energy laboratory (Sluiter A. et al., NREL Analytical Procedure, Google Scholar (2004)). Results for all biomass feedstocks used in this study are provided in Table I below.

TABLE I

Results of biomass analyses.

| | Cellulose = ADF-Lignin [wt %] | Glucan [wt %] | Hemicellulose = NDF-ADF [wt %] | Xylan [wt %] | Mannan [wt %] | Arabinan [wt %] | Lignin [wt %] |
|---|---|---|---|---|---|---|---|
| Mixed Hardwood | 55.8 | 42.8 ± 0.5 | 22.0 | 13.4 ± 0.1 | 1.8 ± 0.01 | 0.6 ± 0.01 | 16.1 |
| Switchgrass | 45.6 | 30.0 ± 3.6 | 27.3 | 18.4 ± 2.1 | 0.3 ± 0.09 | 2.0 ± 0.3 | 8.6 |
| Big bluestem | 44.4 | 37.6 ± 0.1 | 28.6 | 19.9 ± 0.1 | 0.4 ± 0.01 | 2.4 ± 0.02 | 6.9 |
| Corn stover | 40.6 | 38.5 ± 0.1 | 33.6 | 21.6 ± 0.2 | 0.5 ± 0.02 | 2.6 ± 0.03 | 4.2 |
| Mixed perennial grasses | 41.6 | 36.0 ± 0.3 | 27.0 | 21.5 ± 0.1 | 0.5 ± 0.04 | 2.5 ± 0.03 | 7.0 |

NDF stands for neutral detergent fiber and
ADF stands for acid detergent fiber.
Glucan, xylan, mannan and arabinan measurements are provided with a range representing their 90% confidence interval.

EXAMPLES

General

In specific, non-limiting examples provided herein, hardwood was pretreated at 20 and 40 wt % solids. Switchgrass, corn stover, big bluestem and mixed perennial grasses (a co-culture of big bluestem and switchgrass) were pretreated at 40 wt % solids. Operating temperatures ranged from 150° C. to 250° C., and residence times from 20 seconds to 60 minutes. Following pretreatment, samples were enzymatically hydrolyzed. Total yields were determined for glucose, hemicellulose sugars and two degradation products: furfural and 5-HMF. Response surfaces of yield as a function of temperature and residence time were compared for different moisture contents and biomass species. Pretreatment at 170° C. for 60 minutes resulted in glucose yields of 77%, 73%, and 68% for 20 and 40 wt % solids mixed hardwood and mixed perennial grasses, respectively. Pretreatment at 16.0° C. for 60 minutes resulted in glucan to glucose yields of 81% for switchgrass and 85% for corn stover.

Materials and Methods

Figure 1:
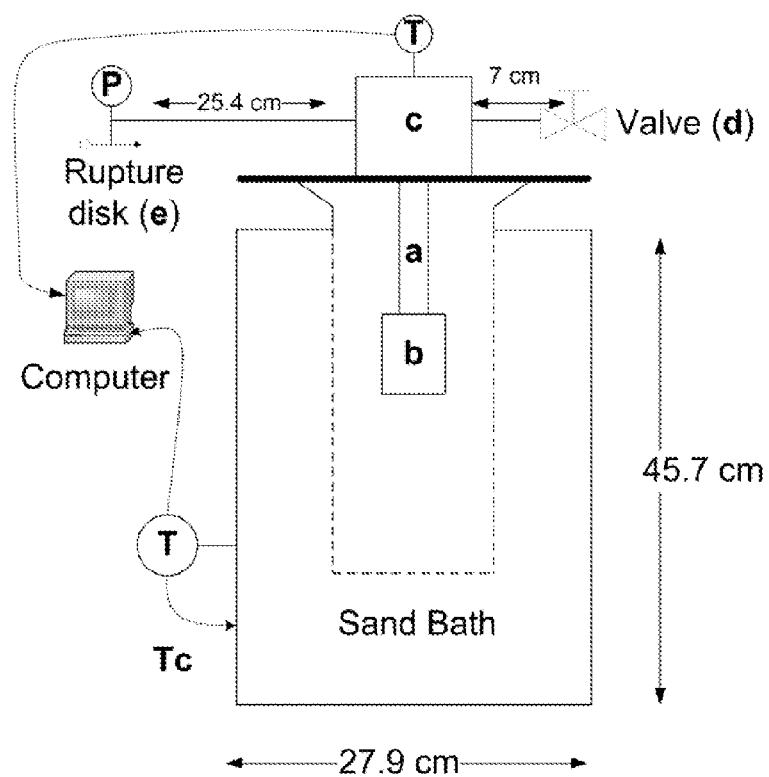
FIG. 1. Diagram of an unstirred 25 mL pretreatment reactor system.

Five different species of biomass were used: mixed hardwood (from NY, harvested in 2007), switchgrass (harvested near Ithaca, N.Y. in fall 2009), mixed perennial grasses (a co-culture of switchgrass and big blue stem harvested near Ithaca, N.Y. in fall 2009), big bluestem grass (harvested near Ithaca, N.Y. in the fall of 2009) and corn stover (obtained from the National Renewable Laboratory, Golden, Colo., in Pretreatment Biomass particles were mixed with deionized water to obtain the desired moisture content (80 or 60 wt % moisture in this study). The resulting slurry (2 g of dry matter and 3 g or 8 g of $H_2O$) was loaded into a stainless steel reactor, which is pictured and described in detail in FIG. 1. The stainless steel pretreatment reactor was made with 20.3 cm (8") of 2.54 cm (1") O.D. (outer diameter) medium pressure tubing (a) and the corresponding end fitting (b) (Autoclave Engineers®, Erie, Pa.). A thermocouple (T) was fed into the top of the reactor and placed 2 cm from the bottom of the reactor in the center of the packed bed of biomass. The top of the reactor was connected to a steel insulation plate and to a 4 way medium pressure fitting (c) that connected to a needle valve (d) (Autoclave Engineers®, Erie, Pa.), a pressure gauge (P) and a rupture disc (e) (ETS, Erie, Pa., pressure rating: 282 bar) using 0.635 cm (¼") O.D. medium pressure tubing (Autoclave Engineers®, Erie, Pa.). This resulted in a nominal reactor volume of 25 ml. The sand bath heaters were controlled by a temperature feedback loop (Tc).

Once closed, the reactor was purged by pressurizing and venting it five times with 30 to 35 bar of $CO_2$. Liquid $CO_2$ was loaded from a siphon tank into the reactor, resulting in a pressure of 60 bar. A fluidized sand bath (Techne®, Burlington, N.J.) was preheated to a temperature of about 100±20° C. above the target reaction temperature. The reactor was then dropped into the sand bath and the bath temperature set 10 to 20° C. above the target reactor temperature. At that point, the pressure rose and reached 200 bar in 20 to 30 seconds. The reactor was, from then on, progressively vented to maintain the reactor at 200±10 bar. The internal reactor temperature reached the target temperature (±5° C.) within 10±1 minutes (typical reactor temperature profiles are given in the supplemental information document). The initial sand bath temperature was chosen to satisfy this condition. Internal reactor temperature was maintained within 5° C. of the target temperature over the course of the residence time. Hence, all residence times reported in this study correspond to the time between the end of the heating period and the transfer of the reactor to an ice bath. Submerging the reactor in the ice bath caused the reactor temperature to drop by 100° C. in about 20 seconds, thus reducing reaction rates to negligible values. The resulting slurry was filtered using Miracloth® filtering cloth (Merck®, Darmstadt, Germany, 38 μm openings) and washed with 1 liter of deionized water.

When the large 1 L stirred reactor was used (as opposed to the small reactor shown in FIG. 1), biomass particles were mixed with deionized water to obtain the desired dry solids content of 40 wt %. The resulting slurry (60 g of dry matter and 90 g of water) was loaded into a 1 L stirred reactor (see FIG. 2). This 1 L stirred reactor consisted of a high-pressure stainless-steel vessel was stirred with a magnetically controlled shaft and impeller (system obtained from Autoclave Engineers®, Erie, Pa.). A custom impeller was machined to optimize biomass mixing throughout the process. Liquid $CO_2$ was delivered from a $CO_2$ siphon tank through a $CO_2$ pump (Thar® Process, Pittsburgh, Pa.) hooked up to a chiller (Thermo-Fisher® Scientific, Waltham, Ma) to avoid $CO_2$ phase change during compression. To maximize $CO_2$ distribution upon entry, it was delivered through a porous metal diffuser that was supplied with the reaction system. A colloidal cooling coil (supplied with the reaction system) was hooked up to the building water through a valve to enable rapid cooling of the reactor. An electrical heating jacket was used for temperature control. Pressure was maintained at the target pressure with a backpressure regulator (BPR, Tescom®, Elk River, Minn.). Heating tape (Omega Engineering®, Stamford, Co) was used to prevent excessive cooling of the BPR during $CO_2$ decompression.

The reactor was purged of air by pressurizing it with $CO_2$ to obtain a pressure of 20 bar, venting it, and repeating this procedure five times. Liquid $CO_2$ was then loaded from a siphon tank into the reactor resulting in a pressure of about 60 bar. An electric heating jacket was used to heat the reactor up to the target temperature using a proportional, integral and differential controller equipped with the Watchtower® software supplied by Autoclave Engineers® (Erie, Pa.). Temperature and pressure were recorded using the same software. The reactor was progressively vented to maintain the reactor at 200±10 bar using a backpressure regulator (BPR). Water losses were considered to be negligible due to the gas exiting at room temperature (saturation concentrations of water in $CO_2$ are low at such conditions; (Duan Z. et al., Chemical geology 193:257-271 2003)). The target temperature (±5° C.) was reached in the reactor after 30 to 45 minutes of heating (typical reactor temperature profiles are given in the supplemental information). All residence times reported in this study correspond to the time at which the reactor was within 5° C. of the target temperature. The reaction was stopped by flowing water through a cooling coil within the reactor. Once the cooling water valve was opened, the reactor temperature typically dropped below 100° C. in about 1 minute, which reduced reaction rates to negligible values.

When a second stage of pretreatment was performed, additional $CO_2$ was loaded into the reactor with the pump to compensate for $CO_2$ vented during the first stage. Once heating was initiated, pressure was maintained at 200±10 bar similarly to the first stage. Heating to the target temperature, subsequent temperature control and cooling were also performed in the same way as the initial stage. Once all of these stages were complete, the resulting biomass was washed and filtered using Miracloth® filtering cloth (Merck®, Darmstadt, Germany, 38 μm openings) and 1 L of deionized water.

Enzymatic Hydrolysis

The washed solids were hydrolyzed in a 1 wt % cellulose solution of 0.05M sodium citrate with 15 FPU/(g cellulose) of spezyme CP® cellulases, 30 (mg protein)/(g cellulose) of Multifect® xylanase (both from Genecor, Copenhagen, DK) and 30 CBU/(g cellulose) of Novo 188® β-glucosidase (Novozyme, Davis, Ca). Cyclohexamide (30 mg/L) and Tetracycline (40 mg/L) were added to prevent growth. A mass balance was carried out to determine cellulose content by assuming that no cellulose was lost during pretreatment. Samples of 150 μL were taken at 4, 24, 72 and 144 hr. Hydrolysis was ended by heating the samples at 95° C. for 5 minutes in a microplate heating block.

To determine the amount of oligomers in the pretreatment liquids, 10 mL of 0.05M sodium citrate buffer with 2 ml of pretreatment liquid, 0.01 FPU/mL of spezyme CP, 0.02 CBU/mL of Novo188 β-glucosidase and 0.03 mg/mL of Multifect® xylanase protein were incubated at 50° C. for 72 hours. For the experiments performed with the 1 L stirred reactor, an alternate oligomer assay was used (Sluiter A. et al., NREL Analytical Procedure. Google Scholar (2004)). Sulfuric acid was added to obtain a 4 wt % acid solution and the resulting solution was heated to 121° C. in a bench-top autoclave (VWR, West Chester, Pa.) for 1 hour to depolymerize the oligosaccharides. Sugar controls (containing comparable amounts of glucose and xylose) were treated in a similar fashion to correct for degradation. The product was then neutralized with calcium carbonate and filtered for analysis. However, both oligomer assays led to statistically equivalent results. All enzymatic hydrolysis experiments were carried out in triplicates in order to calculate a 90% confidence interval for the results (Bobleter O., Progress in Polymer Science 19:797-841 (1994); Kim K. et al., Bioresource Technology 77:139-144 (2001); Mittal et al., Chemical Engineering Science 64:3031-3041 (2009)).

Liquid Analysis

Pretreatment liquids, enzymatic hydrolysis samples, and the samples resulting from the oligomer assay were analyzed for glucose, xylose, mannose, arabinose, furfural and 5-hydroxymethylfurfural (5-HMF) using a Shimadzu liquid chromatography system (Shimadzu, Kyoto, Japan) with an Aminex P-Column (Biorad, Hercules, Calif.). Standards for the analysis were purchased from Sigma-Aldrich (St. Louis, Mo.).

Yield

Concentrations of glucose, xylose, mannose, arabinose, furfural, and 5-HMF were measured during pretreatment and enzymatic hydrolysis using liquid chromatography to calculate yield. Yield coefficients, $Y_i$, are reported as the molar percentage of the maximal possible output of this compound during pretreatment and after 72 hr of enzymatic hydrolysis:

$$Y_g = \frac{Mo_{g,Pr} + Mo_{g,E} + Mo_{g,Ol}}{P_g} \times 100$$

-continued $$Y_h = \frac{Mo_{x,Pr} + Mo_{x,E} + Mo_{x,Ol} + Mo_{m,Pr} + Mo_{m,E} + Mo_{m,Ol} + Mo_{a,Pr} + Mo_{a,E} + Mo_{a,Ol}}{P_x + P_m + P_a} \times 100$$

$$Y_5 = \frac{Mo_{5,Pr}}{P_x + P_a} \times 100$$

$$Y_f = \frac{Mo_{f,Pr}}{P_g + P_m} \times 100$$

The variables $Mo_{i,j}$ and $P_i$ designate moles of monomers or polymers of compound i obtained during process j. The subscripts g, h, x, in, a, 5 and f designate glucose, hemicellulose sugars (i.e. xylose, mannose and arabinose), xylose, mannose, arabinose, 5-HMF or furfural, respectively. The subscripts Pr, E and Ol designate compounds obtained during pretreatment (Pr), 72 hrs of enzymatic hydrolysis (E) or the oligomer assay (Ol), respectively. Glucose and, to a far lesser extent, xylose, can produce degradation products besides 5-HMF and furfural, and all degradation products can further degrade, especially at temperatures close to 240° C. (Bonn G. et al., Journal of Radioanalytical and Nuclear Chemistry 79:171-177 (1983); Dunlop AP, Industrial & Engineering Chemistry 40:204-209 (1948)). However, these products are still a good indicator of sugar degradation during pretreatment.

Losses of reactant mass (water and biomass) after pretreatment (typically between 4 and 9%) are neglected for the purpose of yield calculations. Indeed, these losses do not correlate with temperature and extent of pretreatment and are thus assumed to be due to evaporation, losses during material transfer, and biomass sticking to the reactor walls. In some cases, specifically when switchgrass was pretreated at high temperature (210° C.) for long times (6 minutes or more), mass losses exceeded 10 wt % (up to 17%). In such cases, any mass loss beyond 10 wt % is taken into account in yield calculations.

Hardwood Pretreatment 20 wt % Pretreatment and Saccharification

Figures 3A, 3B, 3C, 3D:
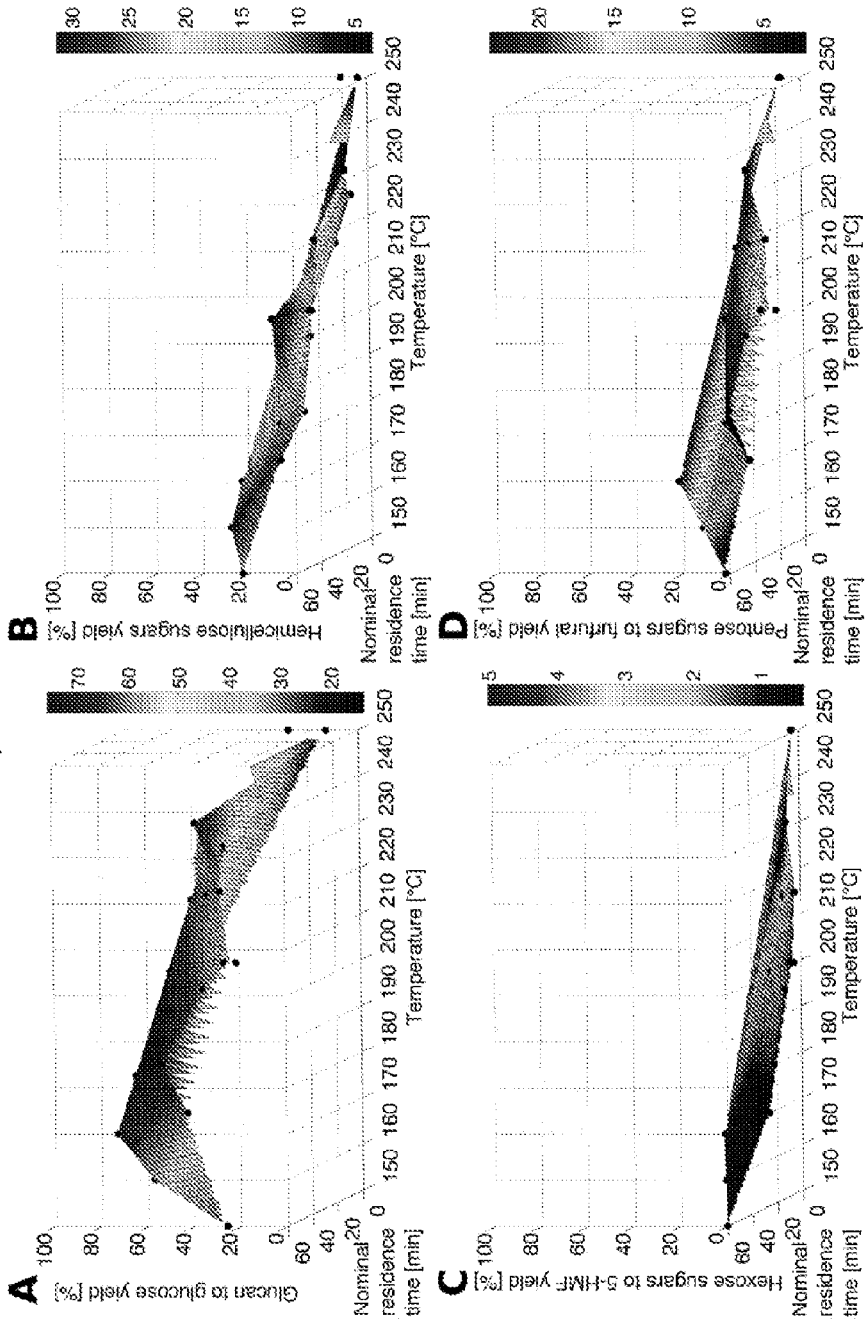
FIGS. 3A-3D. Graphs showing combined yields from pretreatment of a 20 wt % solids (biomass water mixture) slurry of mixed hardwood as a function of pretreatment time and temperature at 200 bar. Yields were obtained after 72 hours of enzymatic hydrolysis (15 FPU/g cellulose or 19.6 FPU/g glucan). (A) Glucan to glucose yields. (B) xylan, arabinan, and mannan (hemicellulose sugars) to xylose, arabinose and mannose yields. (C) Glucan and mannan (pentose sugars) to 5-HMF yields. (D) Xylan and arabinan (hexose sugars) to furfural yields.

The 20 wt % solids slurry of hardwood was pretreated at temperatures between 150° C. and 200° C. and residence times between 20 seconds and 60 minutes. The highest measured $Y_g$ obtained after enzymatic hydrolysis of pretreated hardwood was between 75 and 77% (FIG. 3A). All three $Y_g$ measurements in this range were statistically equivalent with values differing by 2 to 3.6 percentage points. The highest yields were obtained in a temperature range of 170° C. to 180° C. with residence times of 20 to 60 minutes. After 4 hours of enzymatic hydrolysis, yields reached 53 to 68% of their 72 hour yield ($Y_g$) for pretreatment temperatures above 170° C. For 170° C. and below, yields reached between 39% and 47% of their 72 hour value after 4 hours. At pretreatment temperatures below 200° C., between 90% and 95% of the glucose measured and used to calculate $Y_g$ was produced during enzymatic hydrolysis. For temperatures of 225° C. to 230° C., and for 250° C., enzymatic hydrolysis was responsible for 83% to 88%, and 56 to 75%, of the total glucose produced, respectively. These results are corroborated by the increased mass loss with increasing temperature that occurred during pretreatment (from 6% at 150° C. and 1 hour residence time to almost 80% at 250° C. and 1 minute residence time). This result is consistent with the glucan depolymerization reported by Bobleter O., Progress in Polymer Science, 19:797-841 (1994) for temperatures above 220° C.

As shown in FIG. 3B, $Y_h$ values increased almost linearly with temperature up to a value of 28±1% for 160° C. and 60 minutes before dropping down at 150° C. However, the $Y_h$ of 31±5% was obtained at 200° C. and a residence time of 20 minutes. Between 60% and 90% of the hemicellulose sugar yield was due to sugars released during enzymatic hydrolysis. This range narrowed between 63% to 68% for pretreatment temperatures below 200° C., thus demonstrating that at higher temperatures a large fraction of hemicellulose sugars released during pretreatment had degraded.

FIG. 3C shows that a relatively small amount of 5-HMF is produced in all experiments, with at most 4-5% being produced for a pretreatment temperature of 215° C. to 230° C. This was due to increased xylose production during pretreatment. Furfural yields up to 23% were observed for pretreatment temperatures of 200° C. and 230° C. with residence times of 20 minutes and 2 minutes, respectively (see FIG. 3D). Consistent with the release during pretreatment of pentose sugars, furfural yields tended to decrease with temperature and residence times, but are low at 250° C., which could be due to rapid decomposition of the furfural itself.

40 wt % Pretreatment and Saccharification

Given the lower yields and higher byproduct formation observed for pretreatment of 20 wt % solids mixtures at temperatures above 200° C., the experimental range was restricted to temperatures between 150 and 200° C. for 40 wt % solids mixtures. The nominal residence times ranged from 5 to 60 minutes.

Figures 4A, 4B, 4C, 4D:
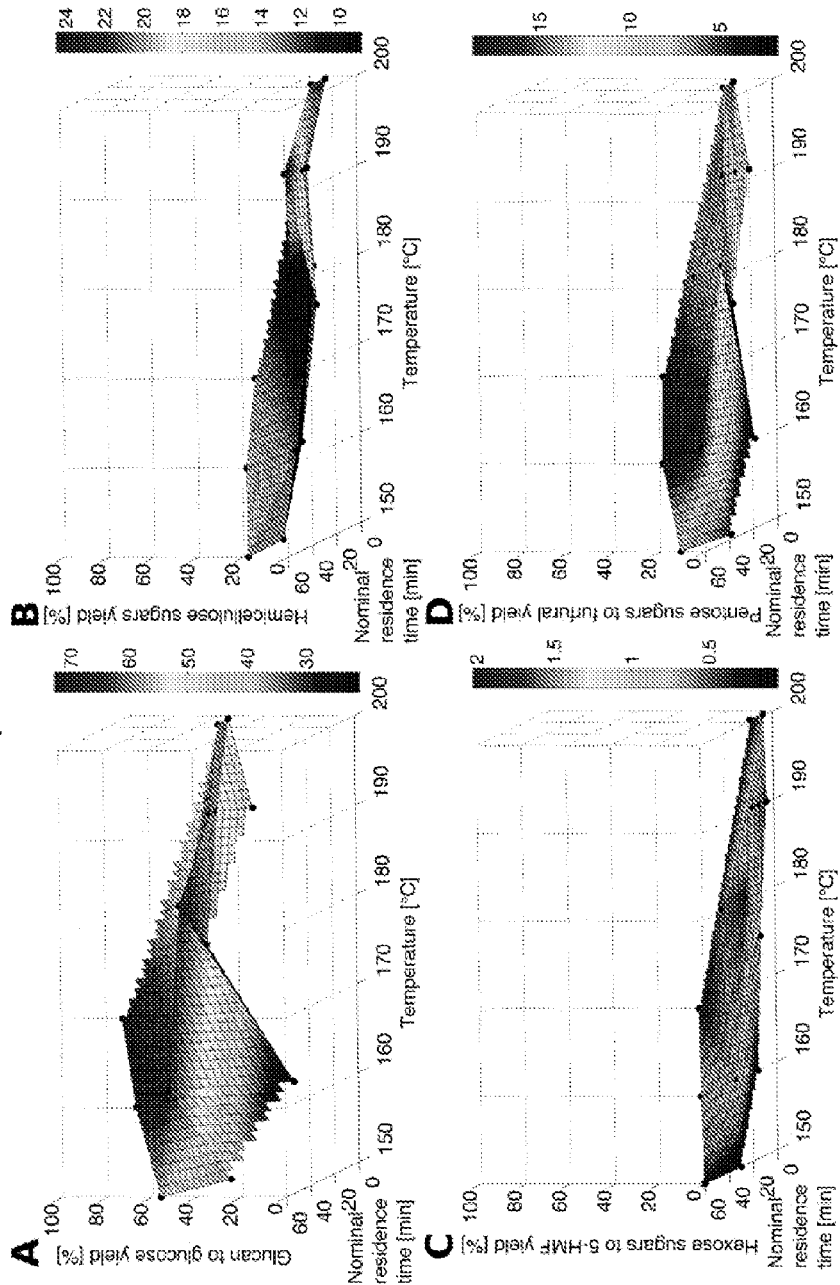
FIGS. 4A-4D. Graphs showing combined yields from pretreatment of a 40 wt % solids (biomass water mixture) slurry of mixed hardwood as a function of pretreatment time and temperature at 200 bar. Yields were obtained after 72 hours of enzymatic hydrolysis (15 FPU/g cellulose or 19.6 FPU/g glucan). (A) Glucan to glucose yields. (B) xylan, arabinan and mannan (hemicellulose sugars) to xylose, arabinose and mannose yields. (C) Glucan and mannan (pentose sugars) to 5-HMF yields. (D) Xylan and arabinan (hexose sugars) to furfural yields.

As shown in FIG. 4A, the highest $Y_g$ was 73±5% for a pretreatment temperature of 170° C. and a nominal residence time of 60 minutes. The three $Y_g$ values reported in the range of 67 to 69% are statistically equivalent suggesting limited sensitivity in the temperature range of 160° C. to 180° C. and retention times of 30 to 69 minutes. Thus, once again, maximal $Y_g$ are observed either at low temperatures and long residence times or higher temperatures with shorter residence times. Between 87% and 95% of $Y_g$ occurred during enzymatic hydrolysis, confirming that very little glucan depolymerization occurs for pretreatment temperatures below 200° C. After 4 hours of enzymatic hydrolysis, yields reached between 78% to 89% of their 72 hr value ($Y_g$) for pretreatment temperatures above 160° C. Below that temperature, yields reached between 53% and 64% of their 72 hour value after 4 hours.

Hemicellulose sugar yields (FIG. 4B) of 18% and 19% were observed for temperatures of 150° C. to 160° C. with residence times of 60 minutes, and a maximum $Y_h$ of 24±5% at 190° C. with a 15 minute residence time. This maximum $Y_h$ coincided with the lowest fraction of sugars released during enzymatic hydrolysis (53%). For other pretreatment conditions, 62% to 85% of $Y_h$ value was produced during enzymatic hydrolysis with no discernable trend. FIG. 4C shows, once again, very low $Y_{5-HMF}$ values indicating limited hexose degradation. Furfural yields, shown in FIG. 4D, increased with temperature and residence time up to values between 15% and 19%.

Switchgrass Pretreatment and Saccharification

Pretreatment of 20 wt % and 40 wt % solids slurries of mixed hardwood led to similar yields. Considering the process advantages linked with higher solid content, the pretreatment runs that followed were only performed with slurries containing 40 wt % dry solids at temperatures between 150° C. and 200° C. with nominal residence times of 5 to 60 minutes.

Glucose yields (FIG. 5A) were the highest for temperatures of 160° C. and 170° C. and a residence time of 60 minutes, with yields of 79% and 81%. As shown in Table II, below, pretreated switchgrass had $Y_g$ values that were eight times larger than the value obtained for untreated biomass. A $Y_g$ of 72% was reached with a pretreatment temperature of 180° C. and a 15 minute residence time. All other yields ranged from 50% to 70%. After 4 hours of enzymatic hydrolysis, yields reached between 80% to 92% of their 72 hour value. For pretreatment temperatures below 200° C., between 92% and 95% of glucose yields were due to glucose released during enzymatic hydrolysis. For a pretreatment temperature of 200° C., the fraction of glucose yields due to enzymatic hydrolysis dropped to between 83% and 87%.

Figures 5A, 5B, 5C, 5D:
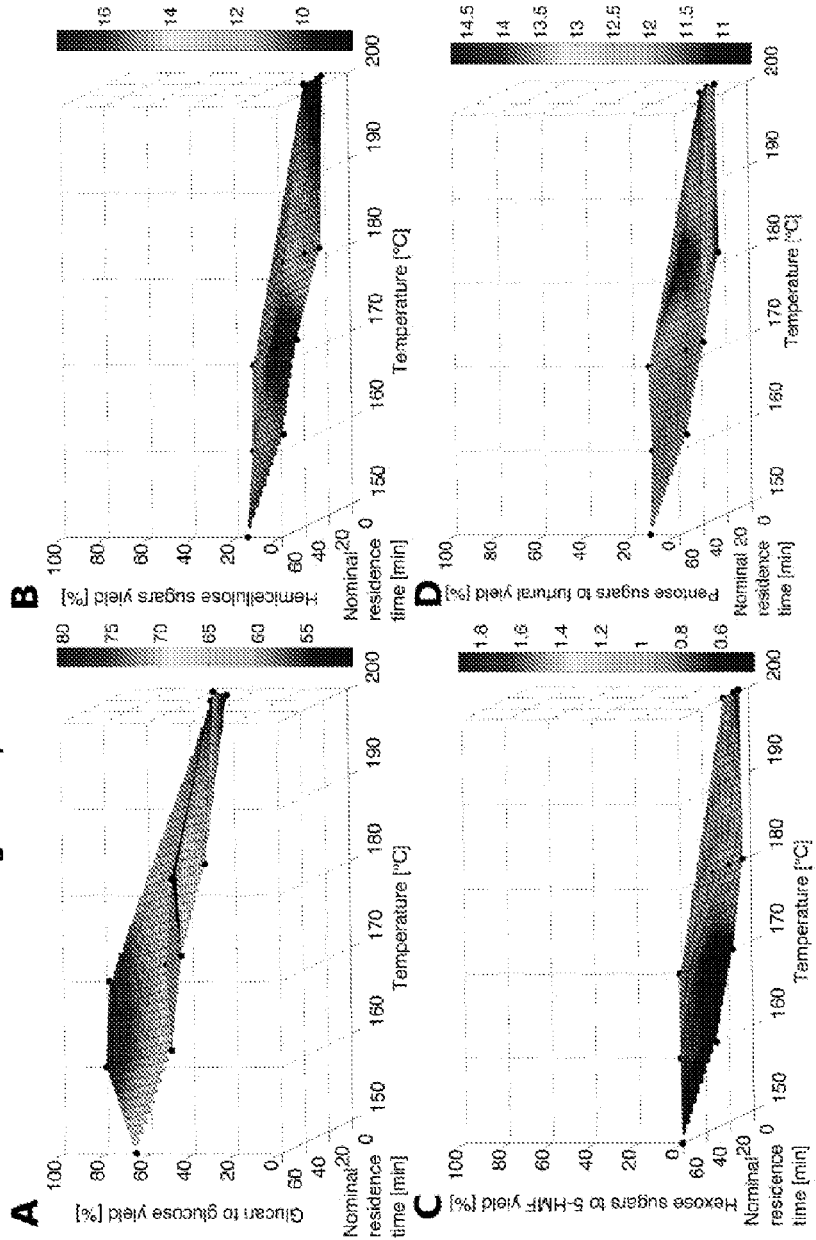
FIGS. 5A-5D. Graphs showing combined yields from pretreatment of a 40 wt % solids (biomass water mixture) slurry of switchgrass as a function of pretreatment time and temperature at 200 bar. Yields were obtained after 72 hours of enzymatic hydrolysis (15 FPU/g cellulose or 22.8 FPU/g glucan). (A) Glucan to glucose yields. (B) xylan, arabinan, and mannan (hemicellulose sugars) to xylose, arabinose, and mannose yields. (C) Glucan and mannan (pentose sugars) to 5-HMF yields. (D) Xylan and arabinan (hexose sugars) to furfural yields.
Figures 6A, 6B, 6C, 6D:
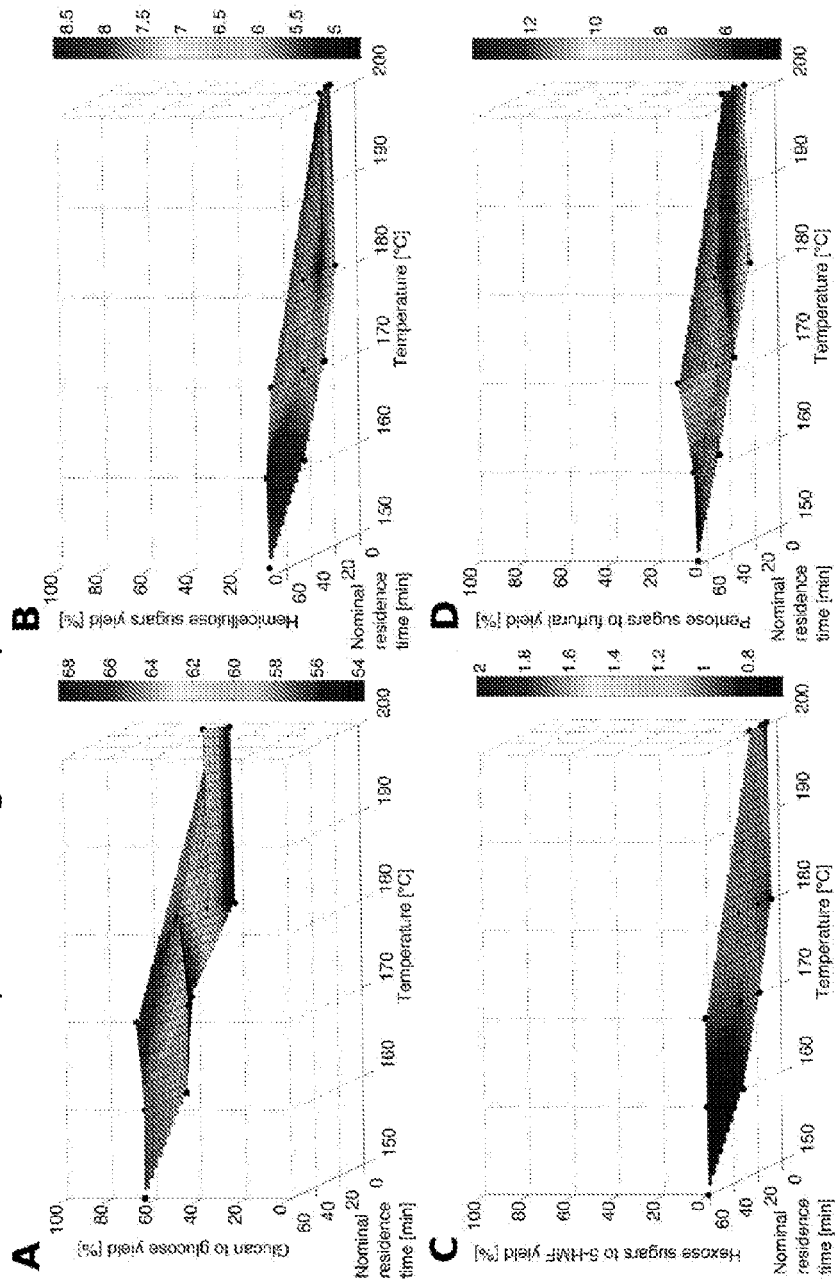
FIGS. 6A-6D. Graphs showing combined yields from pretreatment of a 40 wt % solids (biomass water mixture) slurry of mixed perennial grasses as a function of pretreatment time and temperature at 200 bar. Yields were obtained after 72 hours of enzymatic hydrolysis (15 FPU/g cellulose or 17.3 FPU/g glucan). (A) Glucan to glucose yields. (B) xylan, arabinan and mannan (hemicellulose sugars) to xylose, arabinose and mannose yields. (C) Glucan and mannan (pentose sugars) to 5-HMF yields. (D) Xylan and arabinan (hexose sugars) to furfural yields.

Hemicellulose sugar yields (FIG. 5B) were as high as 16% to 17% for pretreatments at 170° C. with 15 minute and 30 minute residence times, and 150° C. with a residence time of 60 minutes. Other combinations of temperature and residence time led to yields between 9% and 15%. Contribution of sugars released during enzymatic hydrolysis for these combined yields ranged from 62% to 73%. Conversion of hexose sugars to 5-HMF was very limited at all conditions (FIG. 5C). Conversion of pentoses to furfural (FIG. 5D) varied little with temperature and residence time, staying confined to a yield range of 10% to 15%.

degradation, shown in FIG. 6D, ranged from 14% for 180° C. and 15 minutes of pretreatment to 4% for 150° C. and 60 minutes of pretreatment.

Effect of Solids Content

As shown by comparing FIGS. 3A and 4A, changes in biomass solids content appear to have a limited affect on final glucose yields. The variation in $Y_g$ between solids loading of 40 wt % and 20 wt % was consistently under 10 percentage points. Furthermore, the final 72 hour yield was reached earlier with solid loadings of 40 wt %. No significant change in yield occurred after 72 hours of enzymatic hydrolysis. The surfaces depicted in FIGS. 3A and 4A are similar with maximal yields achieved under similar temperature and retention time. However, at the higher solids content, $Y_g$ is less sensitive to temperature. The change in $Y_g$ with temperature for the 20 wt % loading (FIG. 3A) is more dramatic between 170° C. and 150° C. then it is for the 40 wt % loading (FIG. 4A). Heat transfer could be an important cause of this difference. Indeed, a slurry with a higher solid content appeared to lower heat-transfer rates. Thus, it required an initial sand bath temperature that was about 20° C. higher than for the experiments with 20 wt % solids slurries to achieve the same heat-up time. This increased

TABLE II

Results of biomass analyses.

| | No pretreatment | | Pretreatment at 160° C. for 1 hr | | Pretreatment at 70° C. for 1 hr | |
|---|---|---|---|---|---|---|
| | Glucan yield [%] | Hemicellulose sugars yield [%] | Glucan yield [%] | Hemicellulose sugars yield [%] | Glucan yield [%] | Hemicellulose sugars yield [%] |
| Mixed Hardwood (20 wt %) | 5.1 ± 0.3 | 3.9 ± 0.8 | 57 ± 2 | 28 ± 1 | 77 ± 4 | 27 ± 3 |
| Mixed Hardwood (40 wt %) | | | 67 ± 2 | 18 ± 3 | 73 ± 5 | 14 ± 2 |
| Switchgrass | 10.4 ± 0.4 | 6.6 ± 0.4 | 81 ± 1 | 13 ± 1 | 79 ± 1 | 12 ± 1 |
| Big bluestem | 17 ± 1 | 5.0 ± 0.4 | 56 ± 2 | 9.9 ± 0.3 | 66 ± 2 | 13 ± 1 |
| Corn stover | 36 ± 1 | 17 ± 1 | 85 ± 2 | 10 ± 1 | 67 ± 2 | 10 ± 2 |
| Mixed perennial grasses | 12.2 ± 0.4 | 3.5 ± 0.3 | 65 ± 2 | 8.7 ± 0.4 | 68 ± 1 | 6.2 ± 0.3 |

NDF stands for neutral detergent fiber and
ADF stands for acid detergent fiber.
All measurements are provided with a range representing their 90% confidence interval.

Mixed Perennial Grasses Pretreatment and Saccharification

Mixed perennial grasses were pretreated using slurries containing 40 wt % dry solids at temperatures between 150° C. and 200° C. with nominal residence times between 5 and 60 minutes. Experiments were limited to 40 wt % solids for the same reasons as noted for switchgrass experiments.

As shown in FIG. 6A, the highest $Y_g$ value, 68±1%, was observed for pretreatment temperatures of 170° C. with nominal residence times of 15 and 60 minutes. This corresponded to a $Y_g$ value five times greater than the value for untreated biomass (see Table II). After 4 hours of enzymatic hydrolysis, yields had reached between 79% to 86% of their 72 hour yield ($Y_g$). Between 87% and 94% of the glucose reported was released during enzymatic hydrolysis. The highest $Y_h$ value (FIG. 6B) was 9% for a pretreatment temperature of 160° C. and a residence time of 60 minutes. All other yields ranged from 5% to 8%. Once again, conversion of hexose sugars to 5-HMF was very limited at all conditions (FIG. 6C). Furfural yields produced from pentose sandbath temperature could lead to a greater temperature gradient within the reactor, which would have increased the yields for pretreatment experiments at lower temperatures by subjecting part of their mixture to higher temperatures.

Hemicellulose sugar yields, obtained with 40 wt % slurries, are about half those obtained for pretreatment with 20 wt %. However, the response surfaces shown in FIGS. 3B and 4B exhibit similar trends and maxima to the glucose yields. Once again, yields are less sensitive to temperature changes for the higher solids content experiments. Lower $Y_h$ values could be a result of increased pentose sugar degradation or decreased hemicellulose depolymerization during pretreatment. However, neither furfural nor 5-HMF yields significantly increased with the solids content of the slurry. Water limitations and hot spots in the reactor could have led to locally accelerated pyrolysis of hemicellulose. This explanation is consistent with observations of Serapiglia M J et al., Bioenergy Research 2:1-9 (2009), who reported measurable biomass degradation between 175-220° C. for 2 minutes of continuous heating.

Effect of Biomass Species

The biomass species appeared to shift yield numbers (FIGS. 4, 5 and 6) by an approximately constant value. Indeed, yield variations stay essentially the same with different conditions. For example, $Y_g$ values for switchgrass appear to be consistently greater than those of other species by about 10 percentage points regardless of conditions. Yield maxima consistently occur at pretreatment temperatures between 160° C. and 170° C. with a one-hour residence time. Hemicellulose sugars yield was the highest for wood, slightly less for switchgrass, and lower for mixed perennial grasses. Furfural yields show similar variations.

Effect and Stirring and Particle Size in the 1 L Stirred Reactor

Mixed Hardwood Pretreatment

Figure 2:
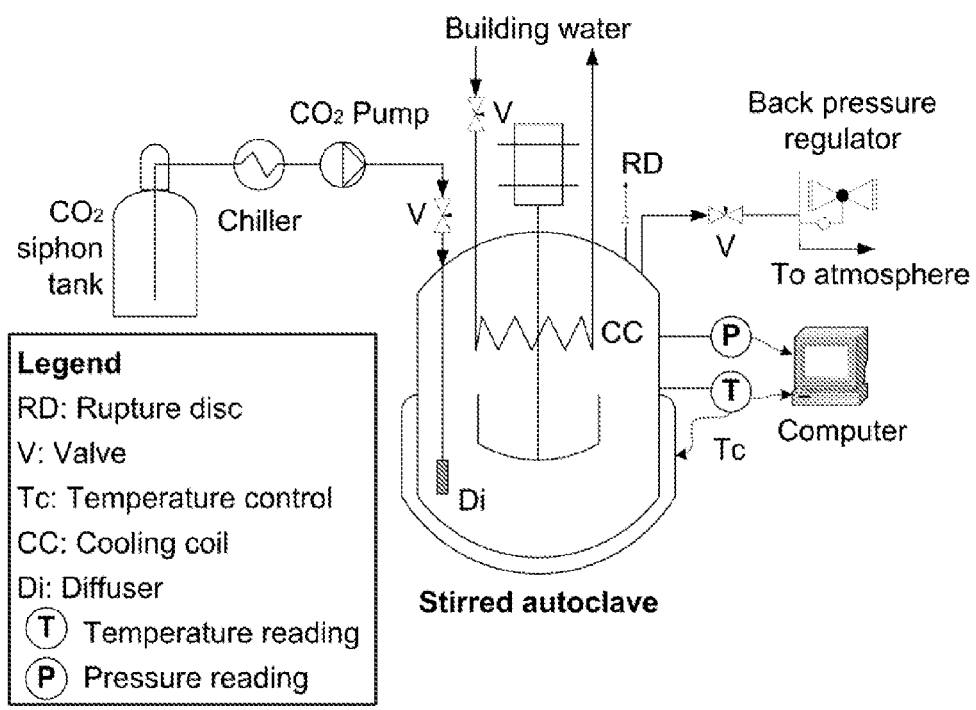
FIG. 2: Diagram of a stirred 1 L pretreatment reactor system.

For further experiments, a 1 L stirred reactor was constructed (shown in FIG. 2). This larger reactor permitted the use of larger biomass particles that have been milled to go through a ⅜ in (0.95 cm) sieve. This particle size corresponds to a more realistic size for industrial use. Mixing greatly reduces any heat gradients that were thought to occur in the small-scale reactor setup and could help limit any pyrolysis effect that could lead to lower monosaccharide recovery.

Figure 7:
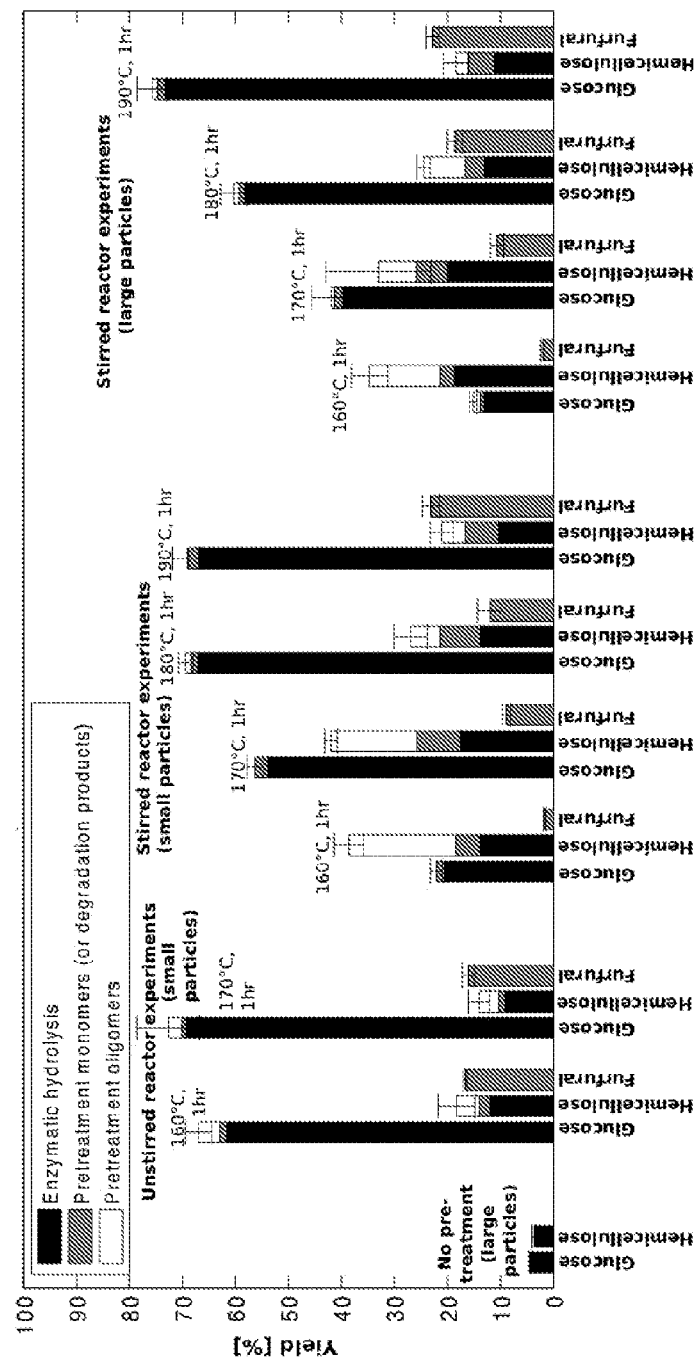
FIG. 7. Bar graph showing yields for single-temperature stage pretreatment of 40 wt % solids (water biomass mixture) mixed hardwood. All yields were obtained after pretreatment (unless no pretreatment is indicated) and 72 hours of enzymatic hydrolysis (15 FPU/gr glucan). Pretreatment was performed at 200 bar, while temperature and residence time are indicated above each set of yields. Bars represent glucan to glucose yields (indicated by "glucose"); xylan, arabinan and mannan to xylose, arabinose and mannose yields (indicated by "hemicellulose"); and xylan and arabinan to furfural yields indicated by "furfural"). The term "unstirred reactor experiments" designates results obtained in the small unstirred reactor. The term "stirred reactor experiments" designates results obtained in the 1 L stirred reactor. The term "large particles" designates results obtained with particles of a size up to or less than 0.95 cm, and the term "small particles" designates results obtained with particles of a size up to or less than 1 mm.

As stated earlier, when 40 wt % solids mixed hardwood was pretreated in the 25 mL unstirred reactor at 160° C. and 170° C. for 60 minutes, glucan to glucose yields ($Y_G$ labeled as "Glucose" in FIG. 7) of 67 and 73% were obtained, and hemicellulose sugars yields ($Y_H$ labeled as "Hemicellulose" in FIG. 7)) of 18 and 14% were obtained. As shown in FIG. 7, when the same small particles (<1 mm) were pretreated in the 1 L stirred reactor at 160° C. and 170° C. for 60 minutes, $Y_G$ decreased from 67 to 22% (160° C.) and from 73 to 57% (170° C.) while $Y_H$ significantly increased to 39 (160° C.) and 42% (170° C.) from values below 20%. However, a $Y_G$ of 69% was obtained both when pretreated at 180° C. and 190° C. for 60 minutes (see FIG. 7).

As discussed in the context of previous results, the foregoing results appear to indicate the presence of temperature gradients in the unstirred system. These gradients lead to higher temperatures in certain areas of the reactor (which increases $Y_G$ compared to the mixed system, which has a more uniform temperature), but they also degrade hemicellulose sugars by creating hot spots within the reactor (which decreases $Y_H$ and increases $Y_F$, which is labeled as "Furfural" in FIG. 7, compared to the mixed system). In addition, it was previously observed that a higher moisture content of 80 wt % (vs. 60 wt % here) led to a quicker drop in $Y_G$ with pretreatment temperature. Thus, it was surmised that a dryer substrate is inclined to increase heat gradients and "flatten" yield variations with temperature. An analogous phenomenon seems to be occurring here, except that gradients are reduced by mixing instead of by increased conductivity of the reactant. To obtain yields similar to those from unstirred reactor while using the 1 L stirred reactor, a temperature of 180° C. or more is preferably applied for 60 minutes, which may indicate that this is, in fact, the average temperature in the unstirred reactor.

When larger particles (i.e., <0.95 cm) were pretreated in the stirred reactor, glucose yields were generally about 10 percentage points lower than those obtained for small particles (i.e., <1 mm) pretreated at identical conditions (see FIG. 7). The only exception was for pretreatment at 190° C. for an hour, which yielded a $Y_G$ of 76%. All hemicellulose sugar yields ($Y_H$) were lower for larger particles while furfural yields ($Y_F$) were roughly equivalent. Therefore, mass transfer limitations due to increased particle size seem to hinder yields and higher temperatures are required to obtain yields similar to those obtained with smaller particles. Finally, it should be noted that pretreated hardwood can achieve dramatically superior glucan and hemicellulose conversion yields to that of untreated hardwood ($Y_G$ is 15 times and $Y_H$ is 8-10 times superior).

Switchgrass Pretreatment

Figure 8:
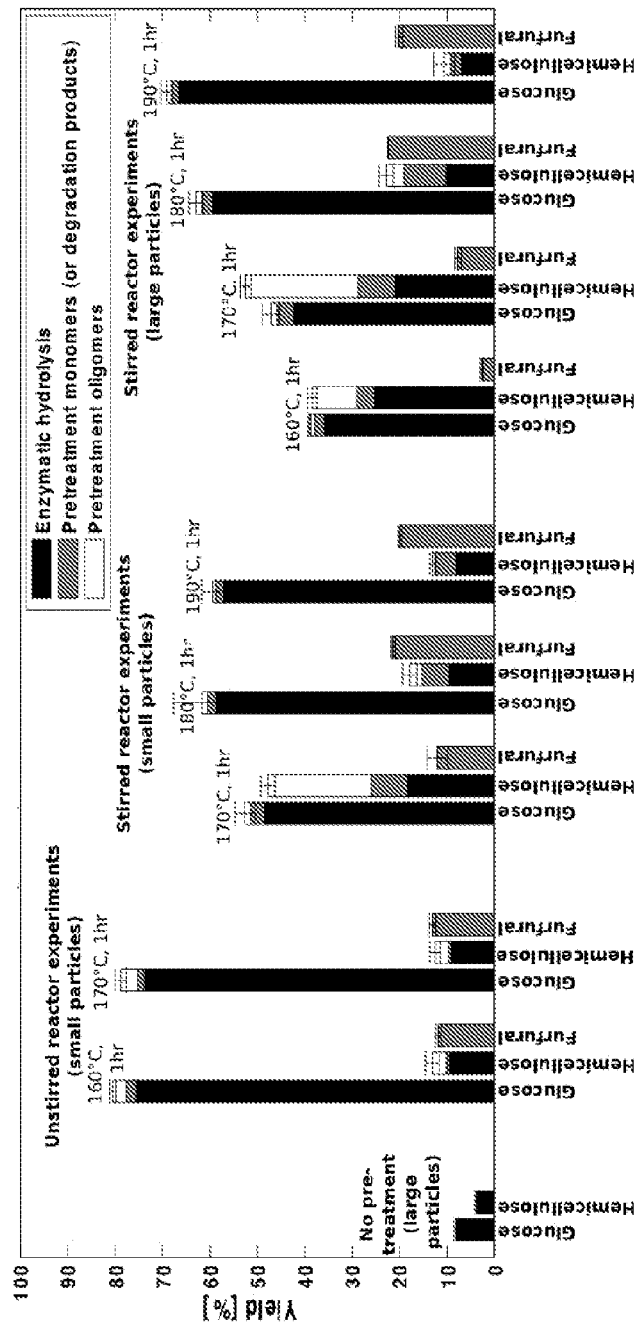
FIG. 8. Bar graph showing yields for single-temperature stage pretreatment of 40 wt % solids (water biomass mixture) switchgrass. All yields were obtained after pretreatment (unless no pretreatment is indicated) and 72 hours of enzymatic hydrolysis (15 FPU/gr glucan). Pretreatment was performed at 200 bar, while temperature and residence time are indicated above each set of yields. Bars represent glucan to glucose yields (indicated by "glucose"); xylan, arabinan and mannan to xylose, arabinose and mannose yields (indicated by "hemicellulose"); and xylan and arabinan to furfural yields indicated by "furfural"). The term "unstirred reactor experiments" designates results obtained in the small unstirred reactor. The term "stirred reactor experiments" designates results obtained in the 1 L stirred reactor. The term "large particles" designates results obtained with particles of a size up to or less than 0.95 cm, and the term "small particles" designates results obtained with particles of a size up to or less than 1 mm.

The various yields obtained in both the unstirred and stirred reactors and using small and large particles are presented in FIG. 8. The use of the stirred reactor consistently led to lower $Y_G$ values compared to the unstirred reactor. However, $Y_H$ values were generally higher, except for temperatures of 190° C. Once again, this result can be attributed to more uniform temperatures in the stirred system.

The $Y_G$ values obtained with smaller particles pretreated in the stirred reactor increased quickly, but quickly leveled off around 60%. However, the $Y_G$ values obtained for the larger particles continually increased with temperature coming within 10 percentage points of those obtained with the unstirred reactor. Hemicellulose sugar yields ($Y_H$) initially increased with temperature until 170° C., after which they dramatically decreased with increasing temperature. The dramatic increase in $Y_H$ is observed with the stirred reactor compared to the unstirred reactor with a pretreatment of 170° C. for 60 minutes (to 48% from 13%), which further indicates the presence of temperature gradients. Furfural yields ($Y_F$) however, were either larger or identical to the unstirred reactor when the stirred reactor was used. Therefore, it seems that the absence of temperature gradients may have decreased the degradation of furfural itself or reduced other forms of hemicellulose degradation, such as pyrolysis.

Results for the Two-Stage Temperature Pretreatment Process

The vast majority of pretreatment experiments in the literature are conducted using a single temperature stage (i.e. one temperature for a given residence time). However, given the typical reaction chemistry of biomass in acidic or neutral media, it may be advantageous to use more than one temperature during pretreatment. Indeed, hemicellulose depolymerization produces oligomers that depolymerize to monomers, which in turn degrade to unwanted byproducts such as furfural (Esteghlalian et al., Bioresource Technology 59:129-136 (1997); Mittal et al., Chemical Engineering Science 64:3031-3041 (2009); Mittal et al., Holzforschung 63:307-314 (2009). The sequential nature of this reaction network entails that furfural production lags behind that of oligo- and monosaccharides. This is particularly apparent in the modeling and experimental results of (Mittal et al., Chemical Engineering Science 64:3031-3041 (2009)) that show that when maple and aspen wood are treated with water at 175° C., xylose and xylo-oligomer concentrations have to increase significantly before furfural starts to appear. The instant invention has attempted to circumvent this problem by using a high pretreatment temperature for a short period during this initial lag in degradation product formation, and then pursue pretreatment for a longer time at lower temperatures, at which monomer degradation is less pronounced (i.e., a short high-temperature stage followed by a longer low-temperature stage).

Mixed Hardwood Pretreatment

Following the reasoning discussed above, two temperature stages were introduced in an attempt to increase $Y_G$ and $Y_H$ values. The approach was to employ a short high-temperature stage (200° C.-210° C. for 0-24 minutes, with 0 minutes representing only the heating phase) followed by a longer low-temperature stage (160-170° C. for 60 minutes)

to pretreat the large (<0.95 cm) hardwood particles. The results are shown in FIGS. 9, 10 and 11.

Figure 9:
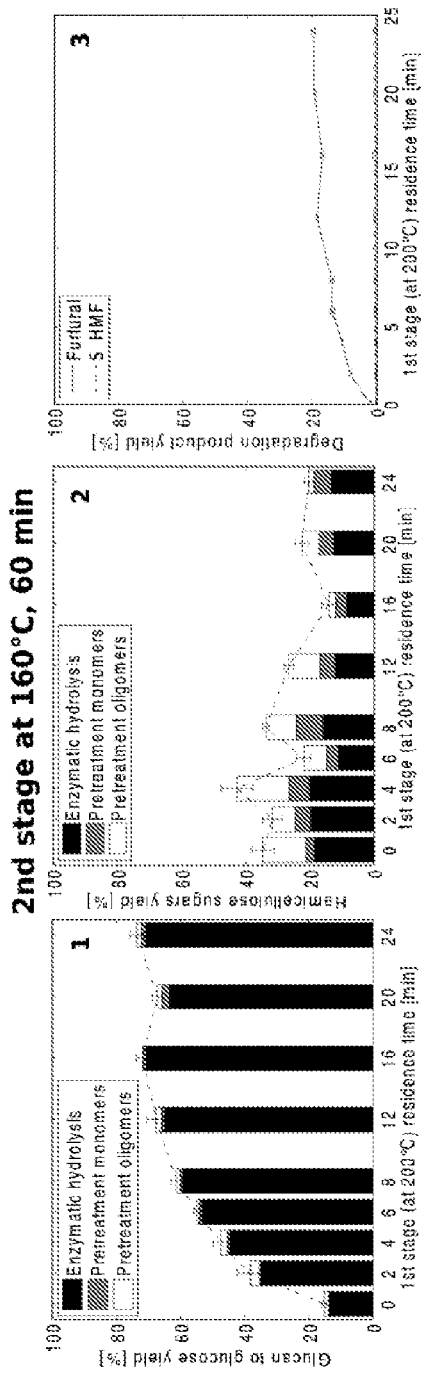
FIG. 9 (parts 1-3). Charts showing yields for two-temperature stage pretreatment of 40 wt % solids (water biomass mixture) large-particle mixed hardwood. All yields were obtained after pretreatment at 200 bar, 200° C. for a varying residence time, and 160° C. for 60 minutes followed by 72 hours of enzymatic hydrolysis (15 FPU/gr glucan).

Glucan to glucose yields consistently increased and plateau once they reached a residence time of about 16 minutes (see FIG. 9, part 1, FIG. 10, part 1 and FIG. 11, part 1). The highest $Y_G$ (83%) was obtained at 210° C. for 16 minutes followed by 160° C. for 60 minutes. Hemicellulose sugar yields ($Y_H$) were more varied with retention time, with a general trend showing a decrease in yield with increasing first stage residence time (see FIG. 9, part 2, FIG. 10, part 2, and FIG. 11, part 2). The highest $Y_H$ were obtained after 4 minutes at 200° C., 1 minute at 200° C., and 8 minutes at 210° C., respectively, with the highest $Y_H$ obtained at 4 minutes at 200° C. and 60 minutes at 160° C. These results suggest that a lower second stage temperature of 160° C. yielded the highest $Y_G$ and $Y_H$ values. In contrast, furfural yields ($Y_F$) increase and then plateau around 8 minutes of high-temperature pretreatment to about 20% regardless of the other parameters (see FIG. 9, part 3, FIG. 10, part 3, and FIG. 11, part 3). Finally, throughout this study, 5-HMF yields ($Y_5$) were insignificant, suggesting very little hexose degradation.

Heating the mixture to 200° C. did not appear to have much of an effect given that the yields for 200° C. for 0 minutes and 160° C. or 170° C. for 60 minutes were quasi-identical to those obtained at 160° C. and 170° C. for 60 minutes (see FIG. 7). Heating to 210° C. had a much more significant effect (more than doubling $Y_G$ and $Y_F$ and significantly increasing $Y_H$). Yields obtained for 210° C., 0 minutes were more or less equivalent to yields for 200° C., 2-4 minutes (followed by 160° C. for 60 minutes in both cases), which corresponds to the time spent at 200±5° C. during the heating phase. Therefore, a couple of minutes spent above 195° C. seems to have a much more significant effect than the 5-10 minutes spent between 150° C. and 195° C.

Following this initial optimization, further tests were performed to determine the effects of modifying the temperature and residence time of the second stage. Therefore, two first stage conditions were chosen, i.e., 210° C. for 1 minute, and 210° C. for 16 minutes. The longer residence time, which was the previously determined optimal time, was selected to explore the effects of a less harsh or slightly modified second stage. The shorter residence time was selected to explore the effect of such a stage with a harsher second stage. The results for these experiments are shown in FIG. 12, with a set of five experiments for the 16 minutes residence time shown on the left and a set of five experiments for the 1 minute residence time shown on the right. In the case of the 16 minute experiments, all three yields reported in FIG. 12 show statistically insignificant changes with the optimal conditions remaining 210° C. for 16 minutes and 160 for 60 minutes. In the case of the 1 minute experiments, most variations of the second stage did not produce significant changes. The only exception was observed for a second stage at 190° C. and 30 minutes for which increases of $Y_G$ to 67% from yields around 50% of $Y_F$ to 20% from values around 10% were observed.

Switchgrass Pretreatment

Given the results for wood, the pretreatment optimization range for switchgrass was reduced to a first stage at 210° C. and a second stage at 160° C. for 60 minutes. Results are shown in FIG. 13. Contrary to wood, the glucan to glucose yields for switchgrass are maximal at short residence times and rapidly decrease as pretreatment time is extended beyond 6 minutes (see FIG. 13, part 1). The maximum observed $Y_G$ was 80% at 210° C. for 1 minute and 160° C. for 60 minute, which was statistically equivalent to the $Y_G$ of 77% obtained with 6 min at 210° C. The heating stage at 210° C. has a more pronounced effect for switchgrass than it does for wood, given that an increase of $Y_G$ by more than 50% is observed when comparing results for 210° C. for 0 minutes (see FIG. 13) and 160° C. for 60 min (see FIG. 8).

Similarly, the results obtained for hardwood, hemicellulose sugar yields ($Y_H$) had a bimodal response when the residence time of the high-temperature stage was varied (see FIG. 13, part 2). Yields of 42% and 27% were obtained after 0 and 4 minutes at 210° C. and 160° C. for 60 minutes, respectively. Furfural yields (see FIG. 13, part 3) rapidly increased to values around 15% after a minute at 210° C. and remained stable, but decreased, for a 12 minute residence time (indicating possible furfural degradation).

Similarly to hardwood, further tests were performed to determine the effects of modifying the temperature and residence time of the second stage. Once again, two first stage conditions were selected, i.e., 210° C. for 0 minutes and 210° C. for 1 minute. The results for these experiments are shown in FIG. 14, with a set of five experiments with a 1 minute residence time shown on the left and a set of five experiments with a 0 minute residence time shown on the right. In the case of the 1 minute experiments, $Y_G$ increased and $Y_H$ decreased with increasing second stage temperature and retention time. This indicates that given the shortness of the first stage, the conditions of the second stage have a more significant impact on the yields. In addition, since a significant proportion of pretreatment reactions occur during the heat-up stage, this variability-prone step may introduce more variability in the final yield. Therefore, a $Y_G$ over 80% is observed when the second stage is brought to 160° C. for 60 minutes as opposed to values around 50% obtained at shorter times or lower temperatures. Similar trends are observed for furfural yields ($Y_F$) and inverse trends are observed for hemicellulose yields ($Y_H$). Less variation was observed when a residence time of 0 minutes at 210° C. was followed by harsher second stage conditions. All values of $Y_G$ were close to 65% while $Y_H$ values reached above 40% for second stages at 160° C. for 60 minutes and 180° C. for 15 minutes while other $Y_H$ values were around 25%.

CONCLUSIONS

Biphasic $CO_2$—$H_2O$ pretreatment in an unstirred reactor, using small (<1 mm) particles, has been shown to produce glucose yields of 73% for wood, 81% for switchgrass, and 85% for corn stover using very similar experimental conditions (i.e., 160-170° C. and a 60 minute residence time), high solid contents (40 wt %) and no additional chemicals. Further improvements were to increase hemicellulose sugars yields and reduce furfural formation by using a mechanically agitated 1 L stirred reactor to increase temperature homogeneity and mass transfer rates. The effect of using larger biomass particles was also explored using the stirred system Subsequently, two-temperature stage pretreatment was introduced to pretreat the same large particles resulting in glucan to glucose conversion yields of 83% for mixed hardwood and 80% for switchgrass. These yields were similar to those obtained using dilute acid pretreatment for wood and within 10% of all major technologies for switchgrass despite the absence of chemical catalysts, the use of larger particles, and the significantly higher solid content (40 wt %).

While there have been shown and described what are at present considered the preferred embodiments of the invention, those skilled in the art may make various changes and modifications which remain within the scope of the invention defined by the appended claims.

What is claimed is:

1. A process for pretreatment of a biomass material, comprising subjecting a biomass material to a biphasic mixture of water and supercritical $CO_2$ under high pressure in a two-stage temperature process wherein an initial short high-temperature stage is conducted at a temperature of at least 200° C. for up to 20 minutes and a subsequent longer low-temperature stage is conducted at a temperature of at least 150° C. and up to 190° C. for 10-120 minutes to provide a pre-treated biomass material, and subjecting the pre-treated biomass material to enzymatic hydrolysis to produce monosaccharides, wherein said enzymatic hydrolysis results in a sugar yield of at least 50% and a furfural yield of no more than 20%.

2. The process of claim 1, wherein said high pressure is at least 74 bar.

3. The process of claim 1, wherein said high pressure is 150-225 bar.

4. The process of claim 1, wherein said high pressure is 190-210 bar.

5. The process of claim 1, wherein said biomass material is selected from the group consisting of hardwood, softwood, grass, hull material, paper products, and combinations thereof.

6. The process of claim 5, wherein said grass is comprised of a perennial grass.

7. The process of claim 6, wherein said perennial grass is selected from switchgrass, big bluestem, miscanthus, alfalfa, orchard grass, and reed canarygrass.

8. The process of claim 5, wherein said hull material is comprised of corn stover.

9. The process of claim 1, wherein said biomass material is a mixture of biomass materials.

10. The process of claim 1, wherein said biphasic mixture is formed by first mixing said biomass material with water to obtain a slurry having a moisture content of at least 10% and not more than 85%, and providing liquid or supercritical $CO_2$ to said slurry in a closed reactor.

11. The process of claim 10, wherein said moisture content is not more than 80%.

12. The process of claim 10, wherein said moisture content is not more than 60%.

13. The process of claim 10, wherein said slurry has a solids content of at least 20 wt %.

14. The process of claim 10, wherein said slurry has a solids content of at least 40 wt %.

15. The process of claim 1, wherein said biphasic mixture is formed by injecting a mixture of water and carbon dioxide into a reactor containing said biomass material, wherein said biomass, before being contacted with said mixture of carbon dioxide and water, has a moisture content of no more than 10%.

16. The process of claim 15, wherein said moisture content is no more than 5%.

17. The process of claim 1, wherein said biphasic mixture is formed by injecting a mixture of water and carbon dioxide into a reactor containing said biomass material, wherein said biomass, before being contacted with said mixture of carbon dioxide and water, has a moisture content of no more than 60%.

18. The process of claim 1, wherein said pre-treatment and said enzymatic hydrolysis are conducted in a reactor in a continuous processing manner.

19. The process of claim 1, further comprising converting said monosaccharides to ethanol, a liquid alkane biofuel, or a commodity starting material.

20. The process of claim 1, wherein said enzymatic hydrolysis results in a furfural yield of no more than 15%.

21. The process of claim 1, wherein said enzymatic hydrolysis results in a furfural yield of no more than 10%.

22. The process of claim 1, wherein said enzymatic hydrolysis results in a furfural yield of no more than 5%.

23. The process of claim 1, wherein said initial short high-temperature step is conducted at a temperature of at least 210° C. for up to 20 minutes.

24. The process of claim 1, wherein said longer low-temperature step is conducted at a temperature of at least 150° C. and up to 180° C. for 30-120 minutes.

25. The process of claim 1, wherein said biomass is a grass, and said initial short high-temperature step is conducted at a temperature of at least 210° C. for up to 5 minutes and said longer low-temperature step is conducted at a temperature of at least 150° C. and up to 180° C. for 30-120 minutes.

26. The process of claim 1, wherein said enzymatic hydrolysis results in a sugar yield of at least 60%.

* * * * *